(12) United States Patent
Kudou et al.

(10) Patent No.: US 8,802,869 B2
(45) Date of Patent: Aug. 12, 2014

(54) 3-HYDROXY-6H-BENZO [C] CHROMENE-6-ONE DERIVATIVE AND MANUFACTURING METHOD THEREOF

(75) Inventors: Kazuhiro Kudou, Ikoma (JP); Noriyoshi Yamamoto, Ikoma (JP); Masakazu Ban, Ikoma (JP); Atsushi Ohno, Ikoma (JP)

(73) Assignee: Santen Pharmaceutical Co., Ltd., Osaka-shi, Osaka (JP)

( * ) Notice: Subject to any disclaimer, the term of this patent is extended or adjusted under 35 U.S.C. 154(b) by 0 days.

(21) Appl. No.: 13/982,534

(22) PCT Filed: Feb. 8, 2012

(86) PCT No.: PCT/JP2012/052824
§ 371 (c)(1),
(2), (4) Date: Jul. 30, 2013

(87) PCT Pub. No.: WO2012/108455
PCT Pub. Date: Aug. 16, 2012

(65) Prior Publication Data
US 2013/0310576 A1 Nov. 21, 2013

(30) Foreign Application Priority Data
Feb. 9, 2011 (JP) .................................. 2011-026188

(51) Int. Cl.
*C07D 311/78* (2006.01)

(52) U.S. Cl.
USPC ........................................................ 549/280

(58) Field of Classification Search
USPC ........................................................ 549/280
See application file for complete search history.

(56) References Cited

U.S. PATENT DOCUMENTS

2009/0326009 A1 12/2009 Matsuda et al.

FOREIGN PATENT DOCUMENTS

| WO | WO 2004/073612 | * | 9/2004 |
| WO | WO 2004/073612 A2 | | 9/2004 |
| WO | WO 2007/032556 A1 | | 3/2007 |

OTHER PUBLICATIONS

Sun et al Bioorganic & Medicinal Chemistry Letters (2006), 16(6), 1468-1472.*
International Search Report (PCT/ISA/210) issued on Mar. 19, 2012, by the Japanese Patent Office as the International Searching Authority for International Application No. PCT/JP2012/052824.
Wanying Sun et al., "6H-Benzo[c]Chromen-6-One Derivatives As Selective ERβ Agonists", Bioorganic & Medicinal Chemistry Letters, 2006, vol. 16, No. 6, pp. 1468-1472.
Jaya Pandey et al., "Synthesis and Biological Activities of Some New Dibenzopyranones and Dibenzopyrans: Search for Potential Oestrogen Receptor Agonists and Antagonists", Bioorganic & Medicinal Chemistry, 2004, vol. 12, No. 9, pp. 2239-2249.
Irini Akritopoulou-Zanze et al., "Synthesis and Biological Evaluation of Novel, Selective, Nonsteroidal Glucocorticoid Receptor Antagonists", Bioorganic & Medicinal Chemistry Letters, 2004, vol. 14, No. 9, pp. 2079-2082.
Wei Deng et al., "Amino Acid-Mediated Goldberg Reactions Between Amides and Aryl Iodides", Tetrahedron Letters, vol. 45, 2004, pp. 2311-2315.

* cited by examiner

*Primary Examiner* — Nizal Chandrakumar
(74) *Attorney, Agent, or Firm* — Buchanan Ingersoll & Rooney PC

(57) ABSTRACT

A method of manufacturing a compound or a salt thereof expressed with a formula (III) below, characterized by causing a compound or a salt thereof expressed with a formula (I) below and a compound or a salt thereof expressed with a formula (II) below to react in the presence of carbonate and copper salt or in the presence of hydroxide salt, carbonate, and copper salt.

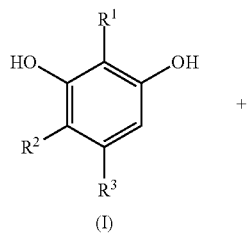

(I)

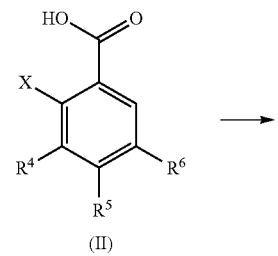

(II)

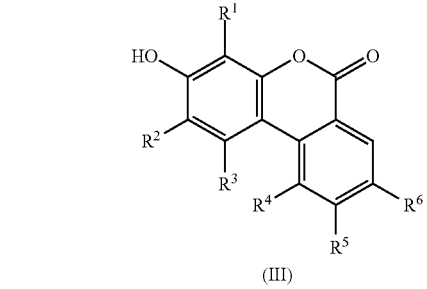

(III)

10 Claims, No Drawings

3-HYDROXY-6H-BENZO [C] CHROMENE-6-ONE DERIVATIVE AND MANUFACTURING METHOD THEREOF

TECHNICAL FIELD

The present invention relates to a 3-hydroxy-6H-benzo [c] hromene-6-one derivative useful as an intermediate product of a 1,2-dihydroquinoline derivative having glucocorticoid receptor binding activities and useful also as a selective estrogen β receptor agonist and a manufacturing method thereof.

BACKGROUND ART

A 6H-benzo [c] chromene-6-one derivative has been known as an intermediate product of a 1,2-dihydroquinoline derivative having glucocorticoid receptor binding activities (for example, see WO2007/032556 (PTD 1)). In addition, the derivative has also been known as a selective estrogen β receptor agonist (see, for example, Bioorganic & Medicinal Chemistry Letters, 16, 2006, 1468-1472 (NPD 1)). NPD 1 describes a method of obtaining a 3-hydroxy-6H-benzo [c] chromene-6-one derivative by causing two equivalents of resorcinol and a bromobenzoic acid derivative to react in water at 100° C. in the presence of two equivalents of sodium hydroxide and a catalyst quantity of copper sulfate.

When the present inventors attempted to manufacture a 3-hydroxy-6H-benzo [c] chromene-6-one derivative with the method described in NPD 1, however, a large amount of by-product was generated, the derivative could not be manufactured at satisfactory yield, and improvement in yield from a point of view of industrial manufacturing was required. For example, in a case where 2-bromobenzoic acid of which position 3 or position 5 was substituted with a nitro group which is an electron-withdrawing group was employed as a bromobenzoic acid derivative, aromatic substitution reaction to a bromo group by a hydroxy group of water or resorcinol proceeded and a target compound could be manufactured only at yield around 10% or less.

CITATION LIST

Patent Document

PTD 1: WO2007/032556

Non Patent Document

NPD 1: Bioorganic & Medicinal Chemistry Letters, 16, 2006, 1468-1472

SUMMARY OF INVENTION

Technical Problem

It is a very interesting task to find a method of manufacturing a 3-hydroxy-6H-benzo [c] chromene-6-one derivative under a mild condition at satisfactory yield and a novel 3-hydroxy-6H-benzo [c] chromene-6-one derivative.

Solution to Problem

The present inventors conducted dedicated studies for achieving the task above, and consequently found a method of manufacturing, by using carbonate and copper salt or by using hydroxide salt, carbonate, and copper salt, a 3-hydroxy-6H-benzo [c] chromene-6-one derivative under a milder condition at more satisfactory yield than with the conventionally known manufacturing method. In addition, the present inventors also found that bubbling of a carbonic acid gas during reaction could be suppressed when hydroxide salt, carbonate, and copper salt were used.

Moreover, the present inventors also found a method of manufacturing the 3-hydroxy-6H-benzo [c] chromene-6-one derivative by causing the 3-hydroxy-6H-benzo [c] chromene-6-one derivative to react with hydroxide salt, to thereby convert the same to 5-acetamide-2-(2,4-dihydroxyphenyl)-benzoic acid which is an open-ring form or a salt thereof, removing such an impurity as copper salt which is an insoluble through a filtering operation, and thereafter causing the resultant product to react with an acid. The manufacturing method is useful in implementing industrial manufacturing, because such an impurity as copper salt which is an insoluble can readily be removed through the filtering operation.

Furthermore, an inexpensive reagent such as sodium carbonate or copper iodide can be applied to the present inventive method, which is cost-effective in implementing industrial manufacturing. Moreover, the present inventors found a novel 3-hydroxy-6H-benzo [c] chromene-6-one derivative and completed the present invention. Namely, the present invention is as set forth below.

The present invention is directed to a method of manufacturing, by causing a compound or a salt thereof expressed with a formula (I) below

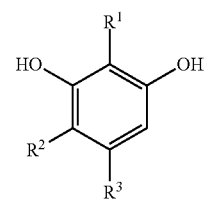

[in the formula (I) above, $R^1$, $R^2$, or $R^3$ representing a hydrogen atom, a lower alkyl group, a hydroxy group, or a lower alkoxy group]

and a compound or a salt thereof expressed with a formula (II) below

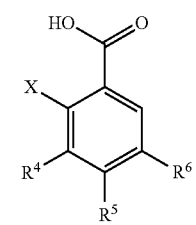

[in the formula (II) above, $R^4$ representing a hydrogen atom, a lower alkyl group, a nitro group, an amino group, or a lower alkylamino group, $R^5$ representing a hydrogen atom or a lower alkyl group, $R^6$ representing a hydrogen atom, a halogen atom, a lower alkyl group, a carboxyl group, a nitro group, or —$NR^aR^b$, $R^a$ and $R^b$ being same or different and representing a hydrogen atom, a formyl group, a lower alkyl carbonyl group, a lower alkenyl carbonyl group, a lower cycloalkyl carbonyl group, an aryl carbonyl group, a carboxyl group, a lower alkoxy carbonyl group, a lower alkenyloxycarbonyl group, a lower cycloalkyloxycarbonyl group, an aryloxy carbonyl group, or an arylalkyloxycarbonyl group, and X representing a halogen atom, a lower alkylsulfonyloxy group, or an aryl sulfonyloxy group]
to react, a compound or a salt thereof expressed with a formula (III) below (III)

[in formula (III) above, $R^1$, $R^2$, $R^3$, $R^4$, $R^5$, or $R^6$ being same in definition in formula (I) and formula (II)],
characterized by causing the compound or the salt thereof expressed with formula (I) above and the compound or the salt thereof expressed with formula (II) above to react in the presence of carbonate and copper salt or in the presence of hydroxide salt, carbonate, and copper salt (hereinafter, the method will be referred to as "the present inventive method").

In addition, the present invention also provides a method of manufacturing, by causing a compound or a salt thereof expressed with a formula (Ia) below (Ia)

and a compound or a salt thereof expressed with a formula (IIa) below (IIa)

[in formula (IIa) above, $R^7$ representing a hydrogen atom, a lower alkyl group, a nitro group, an amino group, or a lower alkylamino group, $R^8$ representing a hydrogen atom or a lower alkyl group, $R^9$ representing a hydrogen atom or a lower alkyl group, $R^{10}$ representing a hydrogen atom, a lower alkyl group, a lower alkenyl group, a lower cycloalkyl group, an aryl group, a hydroxy group, a lower alkoxy group, a lower alkenyloxy group, a lower cycloalkyloxy group, an aryloxy group, or an arylalkyloxy group, and X representing a halogen atom, a lower alkylsulfonyloxy group, or an aryl sulfonyloxy group]
to react, a compound or a salt thereof expressed with a formula (IIIa) below (IIIa)

[in formula (IIIa) above, $R^7$, $R^8$, $R^9$, or $R^{10}$ being same in definition in formula (IIa)],
characterized by causing reaction in the presence of carbonate and copper salt or in the presence of hydroxide salt, carbonate, and copper salt (hereinafter, the method will be referred to as "the present inventive method a").

In addition, the present invention also provides a method of manufacturing, by causing a compound or a salt thereof expressed with a formula (I) below (I)

[in formula (I) above, $R^1$, $R^2$, or $R^3$ representing a hydrogen atom, a lower alkyl group, a hydroxy group, or a lower alkoxy group]
and a compound or a salt thereof expressed with a formula (II) below (II)

[in formula (II) above, $R^4$ representing a hydrogen atom, a lower alkyl group, a nitro group, an amino group, or a lower alkylamino group, $R^5$ representing a hydrogen atom or a lower alkyl group, $R^6$ representing a hydrogen atom, a halogen atom, a lower alkyl group, a carboxyl group, a nitro group, or —$NR^aR^b$, $R^a$ and $R^b$ being same or different and representing a hydrogen atom, a formyl group, a lower alkyl carbonyl group, a lower alkenyl carbonyl group, a lower cycloalkyl carbonyl group, an aryl carbonyl group, a carboxyl group, a lower alkoxy carbonyl group, a lower alkenyloxycarbonyl group, a lower cycloalkyloxycarbonyl group, an aryloxy carbonyl group, or an arylalkyloxycarbonyl group, and X representing a halogen atom, a lower alkylsulfonyloxy group, or an aryl sulfonyloxy group]
to react in the presence of carbonate and copper salt or in the presence of hydroxide salt, carbonate, and a copper salt, a compound or a salt thereof expressed with a formula (III) below

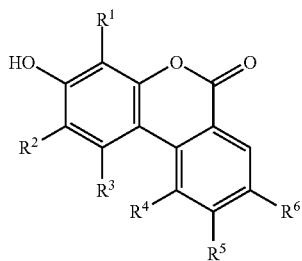

(III)

[in formula (III) above, $R^1$, $R^2$, $R^3$, $R^4$, $R^5$, or $R^6$ being same in definition in formula (I) and formula (II)], characterized by causing the compound or the salt thereof expressed with formula (III) above to react with hydroxide salt for conversion to a compound or a salt thereof expressed with a formula (IV) below

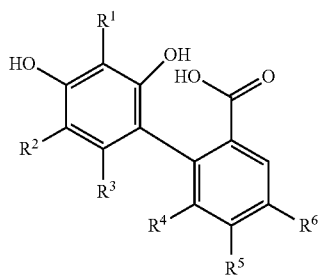

(IV)

[in formula (IV) above, $R^1$, $R^2$, $R^3$, $R^4$, $R^5$, or $R^6$ being same in definition in formula (I) and formula (II)], and then causing the compound or the salt thereof expressed with formula (IV) above to react with an acid (hereinafter, the method will be referred to as "the present inventive method b").

In addition, the present invention also provides a method of manufacturing, by causing a compound or a salt thereof expressed with a formula (Ia) below

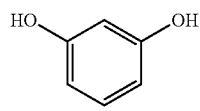

(Ia)

and a compound or a salt thereof expressed with a formula (IIa) below

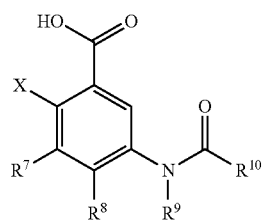

(IIa)

[in formula (IIa) above, $R^7$ representing a hydrogen atom, a lower alkyl group, a nitro group, an amino group, or a lower alkylamino group, $R^8$ representing a hydrogen atom or a lower alkyl group, $R^9$ representing a hydrogen atom or a lower alkyl group, $R^{10}$ representing a hydrogen atom, a lower alkyl group, a lower alkenyl group, a lower cycloalkyl group, an aryl group, a hydroxy group, a lower alkoxy group, a lower alkenyloxy group, a lower cycloalkyloxy group, an aryloxy group, or an arylalkyloxy group, and X representing a halogen atom, a lower alkylsulfonyloxy group, or an aryl sulfonyloxy group] to react in the presence of carbonate and copper salt or in the presence of hydroxide salt, carbonate, and copper salt, a compound or a salt thereof expressed with a formula (IIIa) below

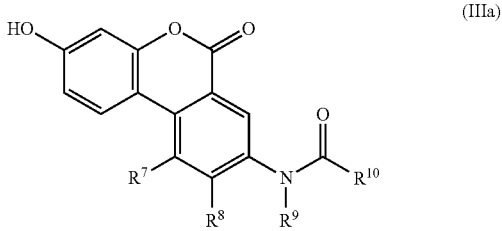

(IIIa)

[in formula (IIIa) above, $R^7$, $R^8$, $R^9$, or $R^{10}$ being same in definition in formula (IIa)]
characterized by causing the compound or the salt thereof expressed with formula (IIIa) above to react with hydroxide salt for conversion to a compound or a salt thereof expressed with a formula (IVa) below

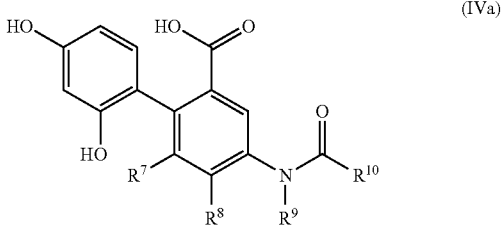

(IVa)

[in formula (IVa) above, $R^7$, $R^8$, $R^9$, or $R^{10}$ being same in definition in formula (IIa)]
and then causing the compound or the salt thereof expressed with formula (IVa) above to react with an acid (hereinafter, the method will be referred to as "the present inventive method c").

In the present inventive method a and the present inventive method c, in formula (IIIa) above, preferably, $R^7$, $R^8$, and $R^9$ each represent a hydrogen atom and $R^{10}$ represents a lower alkyl group, an aryl group, a lower alkoxy group, or an arylalkyloxy group.

In addition, in the present inventive method a and the present inventive method c, in formula (IIIa) above, preferably, $R^7$, $R^8$, and $R^9$ each represent a hydrogen atom and $R^{10}$ represents a methyl group, a phenyl group, a tert-butoxy group, or a benzyloxy group.

In the present inventive method a and the present inventive method c, preferably, the compound or the salt thereof expressed with formula (IIIa) is a compound or a salt thereof selected from the group consisting of
8-acetamide-3-hydroxy-6H-benzo [c] chromene-6-one,
8-benzyloxycarbonylamino-3-hydroxy-6H-benzo [c] chromene-6-one, 8-benzoylamino-3-hydroxy-6H-benzo [c] chromene-6-one, and 8-(tert-butoxycarbonylamino)-3-hydroxy-6H-benzo [c] chromene-6-one.

The carbonate in the present inventive method, the present inventive method a, the present inventive method b, and the present inventive method c is preferably at least any selected from the group consisting of sodium carbonate, ammonium carbonate, potassium carbonate, calcium carbonate, barium carbonate, magnesium carbonate, lithium carbonate, cesium carbonate, copper carbonate, iron carbonate, and silver carbonate.

The copper salt in the present inventive method, the present inventive method a, the present inventive method b, and the present inventive method c is preferably at least any selected from the group consisting of copper chloride, copper bromide, copper iodide, copper carbonate, copper acetate, trifluoroacetic acid copper, copper nitrate, copper sulfate, copper hydroxide, and copper oxide.

In addition, in the present inventive method, the present inventive method a, the present inventive method b, and the present inventive method c, preferably, the carbonate is sodium carbonate and the copper salt is copper iodide.

In addition, in the present inventive method, the present inventive method a, the present inventive method b, and the present inventive method c, preferably, the hydroxide salt is at least any selected from the group consisting of sodium hydroxide, potassium hydroxide, lithium hydroxide, potassium hydroxide, calcium hydroxide, barium hydroxide, and magnesium hydroxide.

In addition, in the present inventive method, the present inventive method a, the present inventive method b, and the present inventive method c, preferably, the hydroxide salt is sodium hydroxide, the carbonate is sodium carbonate, and the copper salt is copper iodide.

In addition, in the present inventive method b and the present inventive method c, the acid is preferably at least any selected from the group consisting of hydrochloric acid, hydrobromic acid, sulfuric acid, nitric acid, benzenesulfonic acid, p-toluenesulfonic acid, acetic acid, and trifluoroacetic acid.

The present invention also provides a compound or a salt thereof expressed with a formula (IIIa) below

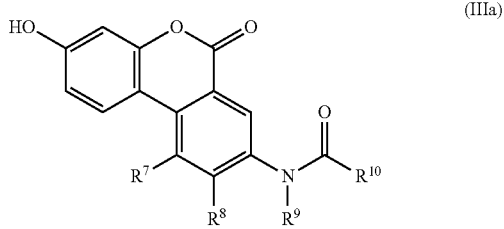

(IIIa)

[in formula (IIIa) above, $R^7$ representing a hydrogen atom, a lower alkyl group, a nitro group, an amino group, or a lower alkylamino group, $R^8$ representing a hydrogen atom or a lower alkyl group, $R^9$ representing a hydrogen atom or a lower alkyl group, $R^{10}$ representing a hydrogen atom, a lower alkyl group, a lower alkenyl group, a lower cycloalkyl group, an aryl group, a hydroxy group, a lower alkoxy group, a lower alkenyloxy group, a lower cycloalkyloxy group, an aryloxy group, or an arylalkyloxy group].

In the compound or the salt thereof according to the present invention, in formula (IIIa) above, preferably, $R^7$, $R^8$, and $R^9$ each represent a hydrogen atom and $R^{10}$ represents a lower alkyl group, an aryl group, a lower alkoxy group, or an arylalkyloxy group.

The compound or the salt thereof according to the present invention is preferably selected from the group consisting of
8-acetamide-3-hydroxy-6H-benzo [c] chromene-6-one,
8-benzyloxycarbonylamino-3-hydroxy-6H-benzo [c] chromene-6-one,
8-benzoylamino-3-hydroxy-6H-benzo [c] chromene-6-one,
8-(tert-butoxycarbonylamino)-3-hydroxy-6H-benzo [c] chromene-6-one,
3-hydroxy-10-nitro-6H-benzo [c] chromene-6-one,
3-hydroxy-9-methyl-6H-benzo [c] chromene-6-one,
8-carboxyl-3-hydroxy-6H-benzo [c] chromene-6-one,
8-iodo-3-hydroxy-6H-benzo [c] chromene-6-one, and
8-bromo-3-hydroxy-6H-benzo [c] chromene-6-one.

Advantageous Effects of Invention

The present invention provides a method of manufacturing a 3-hydroxy-6H-benzo [c] chromene-6-one derivative under a mild condition at satisfactory yield with the use of carbonate and copper salt, or hydroxide salt, carbonate, and copper salt. In addition, in particular in a case of using hydroxide salt, carbonate, and copper salt, bubbling of a carbonic acid gas during reaction can be suppressed. Furthermore, the present invention provides a method of manufacturing the 3-hydroxy-6H-benzo [c] chromene-6-one derivative by causing the 3-hydroxy-6H-benzo [c] chromene-6-one derivative to react with hydroxide salt for conversion to 5-acetamide-2-(2,4-dihydroxyphenyl)-benzoic acid which is an open-ring form or a salt thereof, removing such an impurity as copper salt which is an insoluble through a filtering operation, and thereafter causing the resultant product to react with an acid. Since the manufacturing method can more readily remove such an impurity as copper salt which is an insoluble through a filtering operation, it is useful in implementing industrial manufacturing. In addition, an inexpensive reagent such as sodium carbonate or copper iodide can be applied to such a manufacturing method according to the present invention, and the method is cost-effective in implementing industrial manufacturing. Furthermore, the present invention provides a novel 3-hydroxybenzo [c] chromene-6-one derivative.

DESCRIPTION OF EMBODIMENTS

Definition of the terms (atom, group, ring, or the like) as used herein will be described in detail below. When definition of the following terms is applied mutatis mutandis to definition of another term, it can be applied mutatis mutandis also to a preferred scope of each definition and a particularly preferred scope thereof.

The "halogen atom" refers to a fluorine atom, a chlorine atom, a bromine atom, or an iodine atom.

The "lower alkyl group" refers to a straight-chain or branch alkyl group of which number of carbon atoms is from 1 to 8 and preferably from 1 to 6. A methyl, ethyl, n-propyl, n-butyl, n-pentyl, n-hexyl, n-heptyl, n-octyl, isopropyl, isobutyl, sec-butyl, tert-butyl, or isopentyl group, or the like is exemplified as a specific example.

The "lower alkenyl group" refers to a straight-chain or branch alkenyl group of which number of carbon atoms is from 2 to 8 and preferably from 2 to 6. A vinyl, propenyl, butenyl, pentenyl, hexenyl, heptenyl, octenyl, isopropenyl, 2-methyl-1-propenyl, or 2-methyl-2-butenyl group, or the like is exemplified as a specific example.

The "lower cycloalkyl group" refers to a cycloalkyl group of which number of carbon atoms is from 3 to 8 and preferably from 3 to 6. A cyclopropyl, cyclobutyl, cyclopentyl, cyclohexyl, cycloheptyl, or cyclooctyl group, or the like is exemplified as a specific example.

The "aryl group" refers to a residue obtained by excluding one hydrogen atom from monocyclic aromatic hydrocarbon of which number of carbon atoms is from 6 to 14 or dicyclic or tricyclic condensed polycyclic aromatic hydrocarbon. A phenyl, naphtyl, anthryl, or phenanthryl group, or the like is exemplified as a specific example.

The "arylalkyl group" refers to a group resulting from substitution of a hydrogen atom in a lower alkyl group with an aryl group. A benzyl, phenethyl, or diphenylmethyl group, or the like is exemplified as a specific example.

The "alkoxy group" refers to a group resulting from substitution of a hydrogen atom in a hydroxy group with a lower alkyl group. A methoxy, ethoxy, n-propoxy, n-butoxy, n-pentoxy, n-hexyloxy, n-heptyloxy, n-octyloxy, isopropoxy, isobutoxy, sec-butoxy, tert-butoxy, or isopentoxy group, or the like is exemplified as a specific example.

The "lower alkenyloxy group" refers to a group resulting from substitution of a hydrogen atom in a hydroxy group with a lower alkenyl group. A vinyloxy, propenyloxy, butenyloxy, pentenyloxy, hexenyloxy, ethylpropenyloxy, or methylbutenyloxy group, or the like is exemplified as a specific example.

The "lower cycloalkyloxy group" refers to a group resulting from substitution of a hydrogen atom in a hydroxy group with a lower cycloalkyl group. A cyclopropyloxy, cyclobutyloxy, cyclopentyloxy, cyclohexyloxy, cycloheptyloxy, or cyclooctyloxy group, or the like is exemplified as a specific example.

The "aryloxy group" refers to a group resulting from substitution of a hydrogen atom in a hydroxy group with an aryl group. A phenoxy, naphthoxy, anthryloxy, or phenanthryloxy group, or the like is exemplified as a specific example.

The "arylalkyloxy group" refers to a group resulting from substitution of a hydrogen atom in a hydroxy group with an arylalkyl group. A benzyloxy, phenylethyloxy, 1-naphtylmethyloxy, 1-naphtylethyloxy, 2-naphtylmethyloxy, or 2-naphtylethyloxy group, or the like is exemplified as a specific example.

The "lower alkyl carbonyl group" refers to a group resulting from substitution of a hydrogen atom in a formyl group with a lower alkyl group. A methylcarbonyl, ethylcarbonyl, n-propylcarbonyl, n-butylcarbonyl, n-pentylcarbonyl, n-hexylcarbonyl, isopropylcarbonyl, isobutylcarbonyl, sec-butylcarbonyl, tert-butylcarbonyl, or isopentylcarbonyl group, or the like is exemplified as a specific example.

The "lower alkenyl carbonyl group" refers to a group resulting from substitution of a hydrogen atom in a formyl group with a lower alkenyl group. A vinylcarbonyl, propenylcarbonyl, butenylcarbonyl, pentenylcarbonyl, hexenylcarbonyl, heptenylcarbonyl, octenylcarbonyl, isopropenylcarbonyl, 2-methyl-1-propenylcarbonyl, or 2-methyl-2-butenylcarbonyl group, or the like is exemplified as a specific example.

The "lower cycloalkyl carbonyl group" refers to a group resulting from substitution of a hydrogen atom in a formyl group with a lower cycloalkyl group. A cyclopropylcarbonyl, cyclobutylcarbonyl, cyclopentylcarbonyl, cyclohexylcarbonyl, cycloheptylcarbonyl, or cyclooctylcarbonyl group, or the like is exemplified as a specific example.

The "aryl carbonyl group" refers to a group resulting from substitution of a hydrogen atom in a formyl group with an aryl group. A phenylcarbonyl, naphtylcarbonyl, anthrylcarbonyl, or phenanthrylcarbonyl group, or the like is exemplified as a specific example.

The "lower alkoxy carbonyl group" refers to a group resulting from substitution of a hydrogen atom in a formyl group with a lower alkoxy group. A methoxycarbonyl, ethoxycarbonyl, n-propoxycarbonyl, n-butoxycarbonyl, n-pentoxycarbonyl, n-hexyloxycarbonyl, n-heptyloxycarbonyl, n-octyloxycarbonyl, isopropoxycarbonyl, isobutoxycarbonyl, sec-butoxycarbonyl, tert-butoxycarbonyl, or isopentoxycarbonyl group, or the like is exemplified as a specific example.

The "lower alkenyloxycarbonyl group" refers to a group resulting from substitution of a hydrogen atom in a formyl group with a lower alkenyloxy group. A vinyloxycarbonyl, propenyloxycarbonyl, butenyloxycarbonyl, pentenyloxycarbonyl, hexenyloxycarbonyl, heptenyloxycarbonyl, octenyloxycarbonyl, isopropenyloxycarbonyl, 2-methyl-1-propenyloxycarbonyl, or 2-methyl-2-butenyloxycarbonyl group, or the like is exemplified as a specific example.

The "lower cycloalkyloxycarbonyl group" refers to a group resulting from substitution of a hydrogen atom in a formyl group with a lower cycloalkyloxy group. A cyclopropyloxycarbonyl, cyclobutyloxycarbonyl, cyclopentyloxycarbonyl, cyclohexyloxycarbonyl, cycloheptyloxycarbonyl, or cyclooctyloxycarbonyl group, or the like is exemplified as a specific example.

The "aryloxy carbonyl group" refers to a group resulting from substitution of a hydrogen atom in a formyl group with an aryloxy group. A phenoxycarbonyl, naphthoxycarbonyl, anthryloxycarbonyl, or phenanthryloxycarbonyl group, or the like is exemplified as a specific example.

The "arylalkyloxycarbonyl group" refers to a group resulting from substitution of a hydrogen atom in a formyl group with an arylalkyloxy group. A benzyloxycarbonyl or diphenylmethoxycarbonyl group, or the like is exemplified as a specific example.

The "lower alkylsulfonyl group" refers to a group resulting from substitution of a hydroxy group in a sulfo group with a lower alkyl group. A methylsulfonyl, trifluoromethylsulfonyl, ethylsulfonyl, n-propylsulfonyl, n-butylsulfonyl, n-pentylsulfonyl, n-hexylsulfonyl, isopropylsulfonyl, isobutylsulfonyl, sec-butylsulfonyl, tert-butylsulfonyl, or isopentylsulfonyl group, or the like is exemplified as a specific example.

The "arylsulfonyl group" refers to a group resulting from substitution of a hydroxy group in a sulfo group with an aryl group. A benzenesulfonyl, p-toluenesulfonyl, or naphthalenesulfonyl group, or the like is exemplified as a specific example.

The "lower alkylsulfonyloxy group" refers to a group resulting from substitution of a hydrogen atom in a hydroxy group with a lower alkylsulfonyl group. A methylsulfonyloxy, trifluoromethylsulfonyloxy, ethylsulfonyloxy, n-propylsulfonyloxy, n-butylsulfonyloxy, n-pentylsulfonyloxy, n-hexylsulfonyloxy, isopropylsulfonyloxy, isobutylsulfonyloxy, sec-butylsulfonyloxy, tert-butylsulfonyloxy, or isopentylsulfonyloxy group, or the like is exemplified as a specific example.

The "aryl sulfonyloxy group" refers to a group resulting from substitution of a hydrogen atom in a hydroxy group with an arylsulfonyl group. A benzenesulfonyloxy or p-toluenesulfonyloxy group, or a naphthalenesulfonyloxy group, or the like is exemplified as a specific example.

<Method of Manufacturing 3-Hydroxy-6H-Benzo [c] Chromene-6-One Derivative>

The present invention provides a method of manufacturing, as shown with the following reaction scheme (Synthesis Pathway 1-1), a compound or a salt thereof (a 3-hydroxy-6H-benzo [c] chromene-6-one derivative) expressed with a formula (III) below, characterized by causing a compound or a salt thereof (a 1,3-dihydroxybenzene derivative) expressed with a formula (I) below and a compound or a salt thereof expressed with a formula (II) below to react in the presence of carbonate and copper salt or in the presence of hydroxide salt, carbonate, and copper salt (the present inventive method). According to such a present inventive method, the 3-hydroxy-6H-benzo [c] chromene-6-one derivative can be manufactured under a mild condition at satisfactory yield.

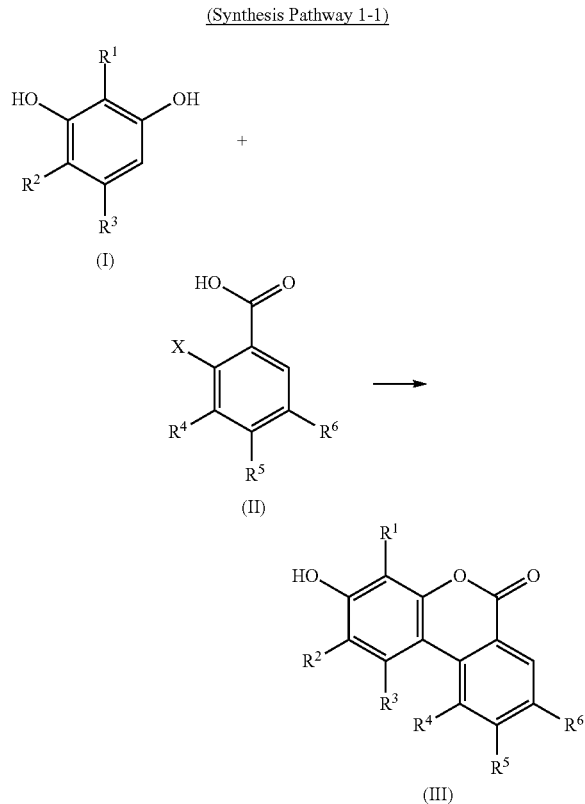

(Synthesis Pathway 1-1)

(I)

(II)

(III)

In formula (I) above, $R^1$, $R^2$, or $R^3$ represents a hydrogen atom, a lower alkyl group, a hydroxy group, or a lower alkoxy group.

In addition, in formula (II) above, $R^4$ represents a hydrogen atom, a lower alkyl group, a nitro group, an amino group, or a lower alkylamino group, $R^5$ represents a hydrogen atom or a lower alkyl group, $R^6$ represents a hydrogen atom, a halogen atom, a lower alkyl group, a carboxyl group, a nitro group, or —$NR^aR^b$, $R^a$ and $R^b$ are same or different and each represent a hydrogen atom, a formyl group, a lower alkyl carbonyl group, a lower alkenyl carbonyl group, a lower cycloalkyl carbonyl group, an aryl carbonyl group, a carboxyl group, a lower alkoxy carbonyl group, a lower alkenyloxycarbonyl group, a lower cycloalkyloxycarbonyl group, an aryloxy carbonyl group, or an arylalkyloxycarbonyl group, and X represents a halogen atom, a lower alkylsulfonyloxy group, or an aryl sulfonyloxy group.

In formula (III) above, $R^1$, $R^2$, $R^3$, $R^4$, $R^5$, or $R^6$ is same in definition in formula (I) above and formula (II) above.

Among the present inventive methods, as shown with the following reaction scheme (Synthesis Pathway 1-2), a method of manufacturing a compound or a salt thereof (a 3-hydroxy-6H-benzo [c] chromene-6-one derivative) expressed with a formula (IIIa) below by causing a compound (resorcinol) or a salt thereof expressed with a formula (Ia) below and a compound or a salt thereof expressed with a formula (IIa) below to react in the presence of carbonate and copper salt or in the presence of hydroxide salt, carbonate, and copper salt (the present inventive method a described above) is preferred.

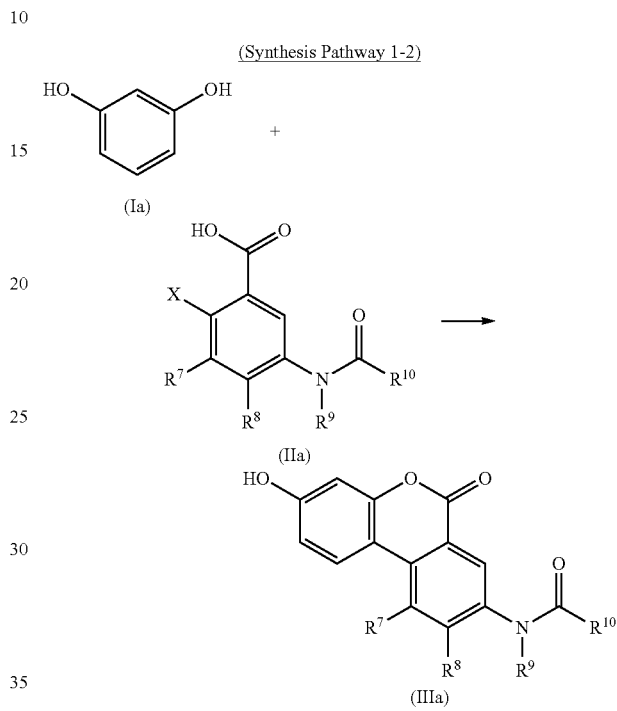

(Synthesis Pathway 1-2)

(Ia)

(IIa)

(IIIa)

In formula (IIa) above, $R^7$ represents a hydrogen atom, a lower alkyl group, a nitro group, an amino group, or a lower alkylamino group, $R^8$ represents a hydrogen atom or a lower alkyl group, $R^9$ represents a hydrogen atom or a lower alkyl group, $R^{10}$ represents a hydrogen atom, a lower alkyl group, a lower alkenyl group, a lower cycloalkyl group, an aryl group, a hydroxy group, a lower alkoxy group, a lower alkenyloxy group, a lower cycloalkyloxy group, an aryloxy group, or an arylalkyloxy group, and X represents a halogen atom, a lower alkylsulfonyloxy group, or an aryl sulfonyloxy group.

In addition, in formula (IIIa) above, $R^7$, $R^8$, $R^9$, or $R^{10}$ is same in definition in formula (IIa) above. In formula (IIIa) above, preferably, $R^7$, $R^8$, and $R^9$ each represent a hydrogen atom and $R^{10}$ represents a lower alkyl group, an aryl group, a lower alkoxy group, or an arylalkyloxy group. In addition, in formula (IIIa) above, more preferably, $R^7$, $R^8$, and $R^9$ each represent a hydrogen atom and $R^{10}$ represents a methyl group, a phenyl group, a tert-butoxy group, or a benzyloxy group. Particularly preferably, the compound or the salt thereof expressed with (IIIa) above is a compound or a salt thereof selected from the group consisting of 8-acetamide-3-hydroxy-6H-benzo [c] chromene-6-one,
8-benzyloxycarbonylamino-3-hydroxy-6H-benzo [c] chromene-6-one,
8-benzoylamino-3-hydroxy-6H-benzo [c] chromene-6-one, and
8-(tert-butoxycarbonylamino)-3-hydroxy-6H-benzo [c] chromene-6-one.

The present invention provides a method of manufacturing, by causing a compound or a salt thereof (a 1,3-dihydroxybenzene derivative) expressed with a formula (I) below and a compound or a salt thereof expressed with a formula (II) below to react in the presence of carbonate and copper salt or in the presence of hydroxide salt, carbonate, and copper salt, a compound or a salt thereof (a 3-hydroxy-6H-benzo [c] chromene-6-one derivative) expressed with a formula (III) below, characterized by causing the compound or the salt thereof expressed with formula (III) below to react with an hydroxide salt for conversion to a compound or a salt thereof expressed with a formula (IV) below and then causing the compound or the salt thereof expressed with formula (IV) below to react with an acid, as shown in the following reaction scheme (Synthesis Pathway 1-3) (the present inventive method b). According to such a present inventive method, the 3-hydroxy-6H-benzo [c] chromene-6-one derivative can be manufactured under a mild condition at satisfactory yield. Then, by using hydroxide salt, carbonate, and copper salt above in reaction to the compound or the salt thereof expressed with formula (II) below, bubbling of a carbonic acid gas during reaction can be suppressed. In addition, by causing the 3-hydroxy-6H-benzo [c] chromene-6-one derivative to react with hydroxide salt for conversion to 5-acetamide-2-(2,4-dihydroxyphenyl)-benzoic acid which is an open-ring form or a salt thereof, such an impurity as copper salt which is an insoluble can readily be removed through a filtering operation. Then, the resultant product is caused to react with an acid, and thus the 3-hydroxy-6H-benzo [c] chromene-6-one derivative can be manufactured.

(Synthesis Pathyway 1-3)

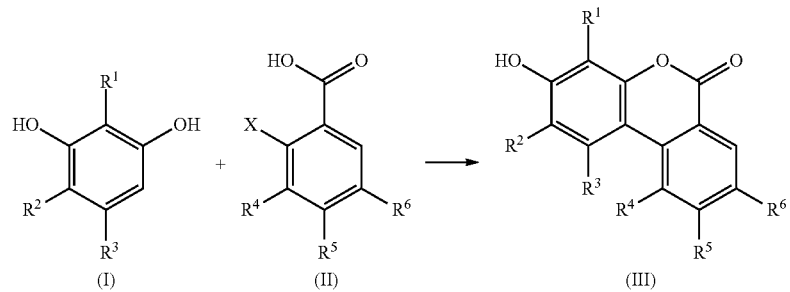

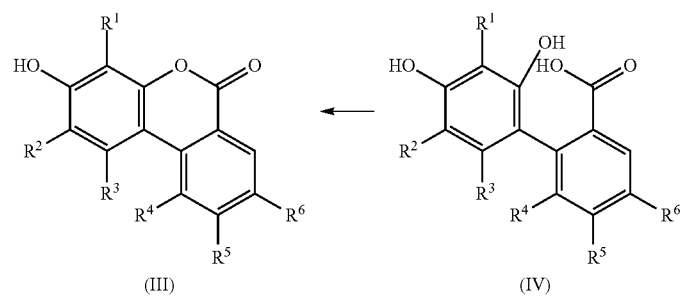

In formula (I) above, $R^1$, $R^2$, or $R^3$ represents a hydrogen atom, a lower alkyl group, a hydroxy group, or a lower alkoxy group.

In addition, in formula (II) above, $R^4$ represents a hydrogen atom, a lower alkyl group, a nitro group, an amino group, or a lower alkylamino group, $R^5$ represents a hydrogen atom or a lower alkyl group, $R^6$ represents a hydrogen atom, a halogen atom, a lower alkyl group, a carboxyl group, a nitro group, or —$NR^aR^b$, $R^a$ and $R^b$ are same or different and each represent a hydrogen atom, a formyl group, a lower alkyl carbonyl group, a lower alkenyl carbonyl group, a lower cycloalkyl carbonyl group, an aryl carbonyl group, a carboxyl group, a lower alkoxy carbonyl group, a lower alkenyloxycarbonyl group, a lower cycloalkyloxycarbonyl group, an aryloxy carbonyl group, or an arylalkyloxycarbonyl group, and X represents a halogen atom, a lower alkylsulfonyloxy group, or an aryl sulfonyloxy group.

In formula (III) above, $R^1$, $R^2$, $R^3$, $R^4$, $R^5$, or $R^6$ is same in definition in formula (I) above and formula (II) above.

Even in the present inventive method b, as shown in the following reaction scheme (Synthesis Pathway 1-4), a method of manufacturing, by causing a compound (resorcinol) or a salt thereof expressed with a formula (Ia) below and a compound or a salt thereof expressed with a formula (IIa) below to react in the presence of carbonate and copper salt or in the presence of hydroxide salt, carbonate, and copper salt, a compound or a salt thereof (a 3-hydroxy-6H-benzo [c] chromene-6-one derivative) expressed with a formula (IIIa) below, characterized by causing the compound or the salt thereof expressed with formula (IIIa) below to react with hydroxide salt for conversion to the compound or the salt thereof expressed with a formula (IVa) below and then causing the compound or the salt thereof expressed with formula (IVa) below to react with an acid (the present inventive method c described above), is preferred.

(Synthesis Pathway 1-4)

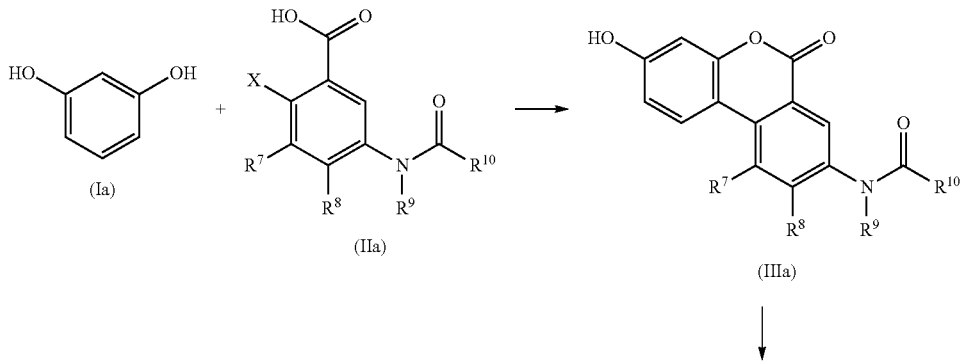

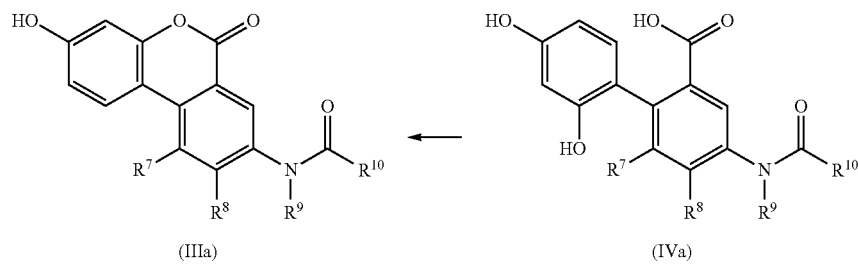

In formula (IIa) above, $R^7$ represents a hydrogen atom, a lower alkyl group, a nitro group, an amino group, or a lower alkylamino group, $R^8$ represents a hydrogen atom or a lower alkyl group, $R^9$ represents a hydrogen atom or a lower alkyl group, $R^{10}$ represents a hydrogen atom, a lower alkyl group, a lower alkenyl group, a lower cycloalkyl group, an aryl group, a hydroxy group, a lower alkoxy group, a lower alkenyloxy group, a lower cycloalkyloxy group, an aryloxy group, or an arylalkyloxy group, and X represents a halogen atom, a lower alkylsulfonyloxy group, or an aryl sulfonyloxy group.

In addition, in formula (IIIa) above, $R^7$, $R^8$, $R^9$, or $R^{10}$ is same in definition in formula (IIa) above. In formula (IIIa) above, preferably, $R^7$, $R^8$, and $R^9$ each represent a hydrogen atom and $R^{10}$ represents a lower alkyl group, an aryl group, a lower alkoxy group, or an arylalkyloxy group. In addition, in formula (IIIa) above, more preferably, $R^7$, $R^8$, and $R^9$ each represent a hydrogen atom and $R^{10}$ represents a methyl group, a phenyl group, a tert-butoxy group, or a benzyloxy group. Particularly preferably, the compound or the salt thereof expressed with (IIIa) above is a compound or a salt thereof selected from the group consisting of 8-acetamide-3-hydroxy-6H-benzo [c] chromene-6-one,
8-benzyloxycarbonylamino-3-hydroxy-6H-benzo [c] chromene-6-one,
8-benzoylamino-3-hydroxy-6H-benzo [c] chromene-6-one, and
8-(tert-butoxycarbonylamino)-3-hydroxy-6H-benzo [c] chromene-6-one.

In the present inventive method, the present inventive method a, the present inventive method b, and the present inventive method c, "in the presence of carbonate and copper salt" means that at least any of carbonate and ions originating from dissociation thereof and at least any of copper salt and ions originating from dissociation thereof should only be present in a system of reaction. In a case where carbonate or copper salt is employed as a source material, both of carbonate and copper salt may be employed as reagents, or any one of carbonate and copper salt may be employed as a reagent. In addition, in a case where carbonate and copper salt which are reagents are allowed to be present in a system of reaction, timing of addition of carbonate and copper salt is not limited only to simultaneous addition. Namely, copper salt may be added after addition of carbonate to a system of reaction, carbonate may be added after addition of copper salt to a system of reaction, or carbonate and copper salt may simultaneously be added.

In the present inventive method, the present inventive method a, the present inventive method b, and the present inventive method c, "in the presence of hydroxide salt, carbonate, and copper salt" means that at least any of hydroxide salt and ions originating from dissociation thereof, at least any of carbonate and ions originating from dissociation thereof, and at least any of copper salt and ions originating from dissociation thereof should only be present in a system of reaction. In a case where hydroxide salt, carbonate, or copper salt is employed as a source material, hydroxide salt, carbonate, and copper salt may be employed as reagents, or at least any one of hydroxide salt, carbonate, and copper salt may be employed as a reagent. In addition, in a case where hydroxide salt, carbonate, and copper salt which are reagents are allowed to be present in a system of reaction, timing of addition of hydroxide salt, carbonate, and copper salt is not limited to simultaneous addition, or the order of addition of reagents is not limited either.

Sodium carbonate, ammonium carbonate, potassium carbonate, calcium carbonate, barium carbonate, magnesium carbonate, lithium carbonate, cesium carbonate, copper carbonate, iron carbonate, silver carbonate, or the like is exemplified as the "carbonate" to be employed in the present inventive method, the present inventive method a, the present inventive method b, and the present inventive method c. It is noted that only one type or two or three types of carbonate may be employed. In addition, valence of a metal element of carbonate is not particularly restricted, and the metal element is from monovalent to trivalent and preferably monovalent or divalent.

Copper halide such as copper chloride, copper bromide, and copper iodide, organic acid copper such as copper carbonate, copper acetate, and trifluoroacetic acid copper, inorganic acid copper such as copper nitrate and copper sulfate, copper hydroxide, copper oxide, or the like is exemplified as the "copper salt" to be employed in the present inventive method, the present inventive method a, the present inventive method b, and the present inventive method c. It is noted that only one type or two or three types of copper salt may be employed. In addition, valence of copper of the copper salt is not particularly restricted, and copper is from monovalent to trivalent and preferably monovalent or divalent.

A case where the carbonate is sodium carbonate and the copper salt is copper iodide is exemplified as particularly preferred combination of carbonate and copper salt in the present inventive method, the present inventive method a, the present inventive method b, and the present inventive method c.

Sodium hydroxide, ammonium hydroxide, potassium hydroxide, calcium hydroxide, barium hydroxide, magnesium hydroxide, lithium hydroxide, or the like is exemplified as the "hydroxide salt" to be employed in the present inventive method, the present inventive method a, the present inventive method b, and the present inventive method c. It is noted that only one or two or three types of hydroxide salt may be employed. In addition, valence of a metal element of hydroxide salt is not particularly restricted, and the metal element is from monovalent to trivalent and preferably monovalent or divalent.

A case where the hydroxide salt is sodium hydroxide, the carbonate is sodium carbonate, and the copper salt is copper iodide is exemplified as particularly preferred combination of hydroxide salt, carbonate, and copper salt in the present inventive method, the present inventive method a, the present inventive method b, and the present inventive method c.

Hydrochloric acid, hydrobromic acid, sulfuric acid, nitric acid, benzenesulfonic acid, p-toluenesulfonic acid, acetic acid, trifluoroacetic acid, or the like is exemplified as the "acid" to be employed in the present inventive method b and the present inventive method c. It is noted that only one type or two or three types of acid may be employed. In addition, valence of the acid is not particularly restricted, and the acid is from monovalent to trivalent and preferably monovalent or divalent.

A molar ratio of carbonate used in the present inventive method, the present inventive method a, the present inventive method b, and the present inventive method c is from 1.00 to 10.0 mole(s), preferably from 2.0 to 5.0 moles, and more preferably from 3.0 to 3.5 moles with respect to 1 mole of the compound or the salt thereof expressed with formula (II) or formula (IIa) above.

In addition, a molar ratio of copper salt used in the present inventive method, the present inventive method a, the present inventive method b, and the present inventive method c is from 0.01 to 5.0 mole(s), preferably from 0.1 to 1.0 mole, and more preferably from 0.2 to 0.5 mole with respect to 1 mole of the compound or the salt thereof expressed with formula (II) or formula (IIa) above.

A molar ratio of hydroxide salt used in the present inventive method, the present inventive method a, the present inventive method b, and the present inventive method c is from 0.30 to 5.00 mole(s), preferably from 0.5 to 2.0 mole(s), and more preferably from 0.8 to 1.2 mole(s) with respect to 1 mole of the compound or the salt thereof expressed with formula (II) or formula (IIa) above.

A molar ratio of acid used in the present inventive method b and the present inventive method c is from 0.80 to 20.0 mole(s), preferably from 3.0 to 15.0 moles, and more preferably from 8.0 to 12.0 moles with respect to 1 mole of the compound or the salt thereof expressed with formula (II) or formula (IIa) above.

At least any of water and an organic solvent is exemplified as a reaction solvent to be employed in the present inventive method, the present inventive method a, the present inventive method b, and the present inventive method c. As an organic solvent, an alcohol-based solvent such as methanol, ethanol, and tertiary butanol, an ether-based solvent such as tetrahydrofuran, 1,4-dioxane, diethyl ether, diisopropyl ether, and 1,2-dimethoxyethane, an amide-based solvent such as N,N-dimethylacetamide, N,N-dimethylformamide, and N-methyl-2-pyrrolidone, an aromatic hydrocarbon-based solvent such as benzene, toluene, and xylene, dimethylsulfoxide, or the like is exemplified. In addition, these can also be used as a mixed solvent. Water, an alcohol solvent, or a mixed solvent of water and an alcohol solvent is exemplified as a preferred reaction solvent, and water, methanol, or a mixed solvent of water and methanol is exemplified as a more preferred reaction solvent.

A reaction time period in the present inventive method, the present inventive method a, the present inventive method b, and the present inventive method c should only be from 30 minutes to 12 hours and preferably from 1 hour to 8 hours.

A reaction temperature in the present inventive method, the present inventive method a, the present inventive method b, and the present inventive method c is in a range from −78° C. to a boiling point of a solvent, preferably in a range from room temperature to 100° C., and more preferably in a range from 25° C. to 70° C.

In addition, in the present inventive method a, preferably, after conversion to the compound or the salt thereof expressed with general formula (IV) above, an insoluble is filtered and then the compound or the salt thereof expressed with general formula (IV) above is caused to react with an acid.

In addition, in the present inventive method c, preferably, after conversion to the compound or the salt thereof expressed with general formula (IVa) above, an insoluble is filtered and then the compound or the salt thereof expressed with general formula (IVa) above is caused to react with an acid.

It is noted that the compound expressed with formula (IIa) above which serves as a source material in the present inventive method a and the present inventive method c can be manufactured, for example, in accordance with a synthesis pathway shown in a reaction scheme as below (Synthesis Pathway 2).

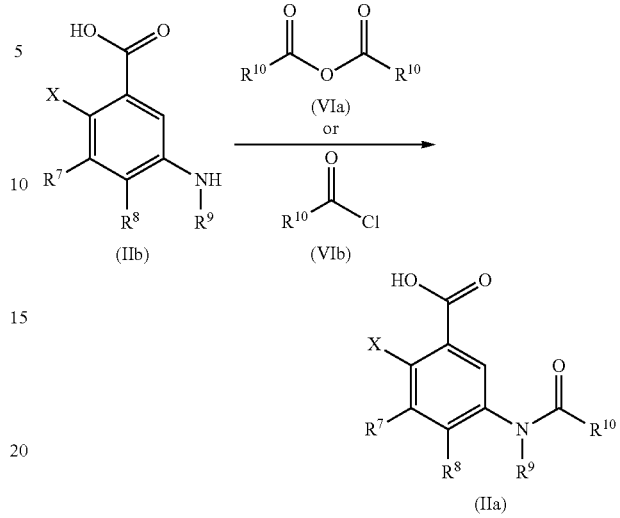

(Synthesis Pathway 2)

Namely, by causing a compound expressed with a formula (IIb) above to react with a compound expressed with a formula (VIa) above or a compound expressed with a formula (VIb) above at room temperature for 2 hours to 12 hours in the presence of a base such as sodium hydroxide or sodium hydrogen carbonate, the compound expressed with formula (IIa) above can be obtained. It is noted that definition of $R^7$, $R^8$, $R^9$, $R^{10}$, and X shown in the reaction scheme above is the same as the definition in formula (IIa) above.

At least any of water and an organic solvent is exemplified as a reaction solvent to be employed in Synthesis Pathway 2 above. As an organic solvent, an alcohol-based solvent such as methanol, ethanol, and tertiary butanol, an ether-based solvent such as tetrahydrofuran, 1,4-dioxane, diethyl ether, diisopropyl ether, and 1,2-dimethoxyethane, an amide-based solvent such as N,N-dimethylacetamide, N,N-dimethylformamide, and N-methyl-2-pyrrolidone, an aromatic hydrocarbon-based solvent such as benzene, toluene, and xylene, dimethylsulfoxide, or the like is exemplified. In addition, these can also be employed as a mixed solvent. Water or an ether-based solvent such as tetrahydrofuran, 1,4-dioxane, diethyl ether, diisopropyl ether, and 1,2-dimethoxyethane is exemplified as a particularly preferred reaction solvent.

In addition, the compound expressed with formula (IIb) above which serves as a source material in Synthesis Pathway 2 above can be manufactured, for example, in accordance with a synthesis pathway shown in a reaction scheme as below (Synthesis Pathway 3).

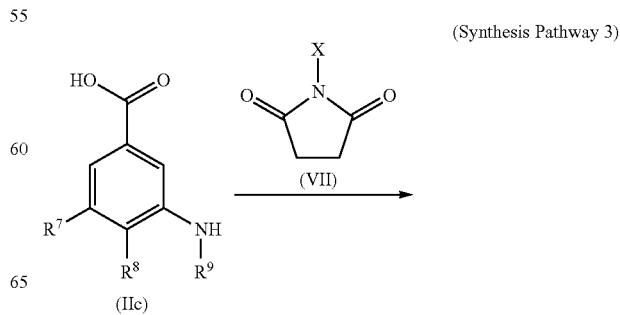

(Synthesis Pathway 3)

-continued

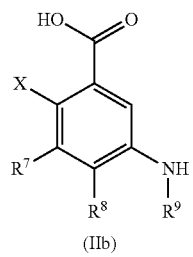

Namely, the compound expressed with formula (IIb) above can be obtained by causing a compound expressed with a formula (IIc) above and a halogenation agent (in a formula (VII) above, X being Cl, Br, or I) to react for 1 hour to 5 hours at 0° C. to 50° C. It is noted that definition of $R^7$, $R^8$, and $R^9$ shown in the reaction scheme above is the same as the definition in formula (IIa) above.

At least any of water and an organic solvent is exemplified as a reaction solvent to be employed in Synthesis Pathway 3 above. As an organic solvent, an alcohol-based solvent such as methanol, ethanol, and tertiary butanol, an ether-based solvent such as tetrahydrofuran, 1,4-dioxane, diethyl ether, diisopropyl ether, and 1,2-dimethoxyethane, an amide-based solvent such as N,N-dimethylacetamide, N,N-dimethylformamide, and N-methyl-2-pyrrolidone, an aromatic hydrocarbon-based solvent such as benzene, toluene, and xylene, dimethylsulfoxide, or the like is exemplified. In addition, these can also be employed as a mixed solvent. An ether-based solvent such as tetrahydrofuran, 1,4-dioxane, diethyl ether, diisopropyl ether, and 1,2-dimethoxyethane or an amide-based solvent such as N,N-dimethylacetamide, N,N-dimethylformamide, and N-methyl-2-pyrrolidone is exemplified as a particularly preferred reaction solvent.

<3-Hydroxy-6H-Benzo [c] Chromene-6-One Derivative>

The present invention also provides a compound or a salt thereof expressed with formula (IIIa) below (a 3-hydroxy-6H-benzo [c] chromene-6-one derivative). Such a 3-hydroxy-6H-benzo [c] chromene-6-one derivative according to the present invention is novel, and it is useful as an intermediate product of a 1,2-dihydroquinoline derivative having glucocorticoid receptor binding activities. In addition, the 3-hydroxy-6H-benzo [c] chromene-6-one derivative according to the present invention is also useful as a selective estrogen β receptor agonist.

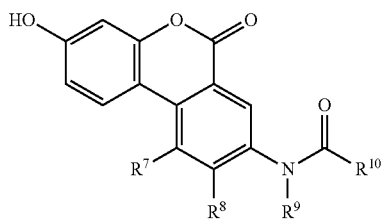

In formula (IIIa) above, $R^7$, $R^8$, $R^9$, or $R^{10}$ is the same as described above. In formula (IIIa) above, preferably, $R^7$, $R^8$, and $R^9$ each represent a hydrogen atom and $R^{10}$ represents a lower alkyl group, an aryl group, a lower alkoxy group, or an arylalkyloxy group. In addition, in formula (IIIa) above, more preferably, $R^7$, $R^8$, and $R^9$ each represent a hydrogen atom and $R^{10}$ represents a methyl group, a phenyl group, a tert-butoxy group, or a benzyloxy group.

A compound or a salt thereof selected from the group below is exemplified as a particularly preferred example of the 3-hydroxy-6H-benzo [c] chromene-6-one derivative according to the present invention:
  8-acetamide-3-hydroxy-6H-benzo [c] chromene-6-one;
  8-benzyloxycarbonylamino-3-hydroxy-6H-benzo [c] chromene-6-one;
  8-benzoylamino-3-hydroxy-6H-benzo [c] chromene-6-one;
  8-(tert-butoxycarbonylamino)-3-hydroxy-6H-benzo [c] chromene-6-one;
  3-hydroxy-10-nitro-6H-benzo [c] chromene-6-one;
  3-hydroxy-9-methyl-6H-benzo [c] chromene-6-one;
  8-carboxyl-3-hydroxy-6H-benzo [c] chromene-6-one;
  8-iodo-3-hydroxy-6H-benzo [c] chromene-6-one; and
  8-bromo-3-hydroxy-6H-benzo [c] chromene-6-one.

The compound expressed with formula (IIIa) above as well as a source material and a reagent employed in the present inventive method, the present inventive method a, the present inventive method b, and the present inventive method c described above may form "salt" with an acid or a base. Specific examples include: salts with an inorganic acid such as hydrochloric acid, hydrobromic acid, hydroiodic acid, nitric acid, sulfuric acid, and phosphoric acid; salts with an organic acid such as carbonic acid, acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate ester, methyl sulfate, naphthalenesulfonic acid, and sulfosalicylic acid; quaternary ammonium salts such as methyl bromide and methyl iodide; salts with a halogen ion such as a bromine ion, a chlorine ion, and an iodine ion; salts with an alkali metal such as lithium, sodium, and potassium; salts with an alkaline earth metal such as calcium and magnesium; salts of a metal such as copper, iron, and zinc; salts with ammonia; salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, or N,N-bis(phenylmethyl)-1,2-ethanediamine; and the like.

In addition, the compound expressed with formula (IIIa) above as well as a source material and a reagent employed in the present inventive method, the present inventive method a, the present inventive method b, and the present inventive method c described above may be in a form of a hydrate or a solvate.

In a case where a geometric isomer or an optical isomer is present in the compound expressed with formula (IIIa) above as well as a source material and a reagent employed in the present inventive method, the present inventive method a, the present inventive method b, and the present inventive method c described above, the isomer is also encompassed within the scope of the present invention.

In a case where a proton tautomerism is present in the compound expressed with formula (IIIa) above as well as a source material and a reagent employed in the present inventive method, the present inventive method a, the present inventive method b, and the present inventive method c described above, the tautomer is also encompassed in the present invention.

In addition, the compound expressed with formula (IIIa) above as well as a source material, a reagent, and a hydrate or a solvate thereof employed in the present inventive method, the present inventive method a, the present inventive method b, and the present inventive method c described above may be a crystal, and in a case where a crystal polymorph and a group of crystal polymorphs (crystal polymorph system) is present in the crystal, those crystal polymorph and group of crystal polymorphs (crystal polymorph system) are also encompassed in the present invention. Here, the group of crystal polymorphs (crystal polymorph system) means a crystal form in each stage in a case where a crystal form variously changes depending on conditions and states for manufacturing, crystallization, storage, and the like of those crystals (the present state including also a formulated state) and the entire process thereof.

Though a method of manufacturing a 3-hydroxy-6H-benzo [c] chromene-6-one derivative according to the present invention is not particularly restricted, the derivative can suitably be manufactured with the present inventive method a or the present inventive method c described above. The 3-hydroxy-6H-benzo [c] chromene-6-one derivative according to the present invention is considered to be manufactured also with a method other than the present inventive method a shown as Synthesis Pathway 1-2 and the present inventive method c shown as Synthesis Pathway 1-4, and such a manufacturing method can be exemplified, for example, by a method as shown with a reaction scheme below (Synthesis Pathway 1-3).

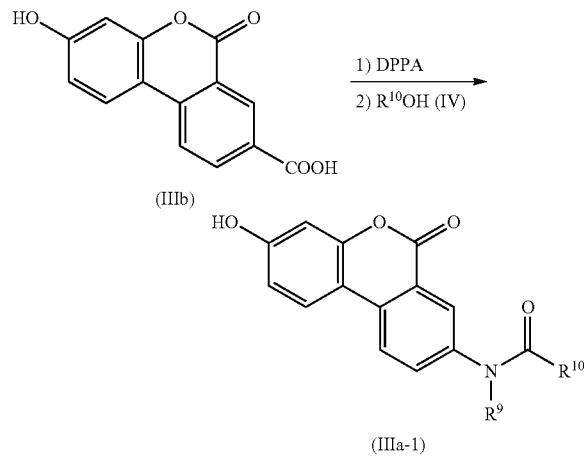

Namely, by causing a compound expressed with a formula (IIIb) (a compound in formula (III) above, in which $R^1$, $R^2$, $R^3$, $R^4$, and $R^5$ are H and $R^6$ is COOH) to react with such a reagent as diphenylphosphoryl azide (DPPA) and further causing the resultant substance to react with such an alcohol as tert-butyl alcohol expressed with formula (IV), a compound expressed with a formula (IIIa-1) (a compound in formula (IIIa) described above, in which $R^7$ and $R^8$ are each H) can be obtained. It is noted that $R^9$ and $R^{10}$ in Synthesis Pathway 1-3 above are the same in definition as in formula (IIa) described above.

At least any of water and an organic solvent is exemplified as a reaction solvent employed in Synthesis Pathway 1-3. As an organic solvent, an alcohol-based solvent such as methanol, ethanol, and tertiary butanol, an ether-based solvent such as tetrahydrofuran, 1,4-dioxane, diethyl ether, diisopropyl ether, and 1,2-dimethoxyethane, an amide-based solvent such as N,N-dimethylacetamide, N,N-dimethylformamide, and N-methyl-2-pyrrolidone, an aromatic hydrocarbon-based solvent such as benzene, toluene, and xylene, dimethylsulfoxide, or the like is exemplified. In addition, these can also be employed as a mixed solvent. An ether-based solvent such as tetrahydrofuran, 1,4-dioxane, diethyl ether, diisopropyl ether, and 1,2-dimethoxyethane, an amide-based solvent such as N,N-dimethylacetamide, N,N-dimethylformamide, and N-methyl-2-pyrrolidone, or an aromatic hydrocarbon-based solvent such as benzene, toluene, and xylene is exemplified as a particularly preferred reaction solvent.

In addition, for example, a method as shown with a reaction scheme below (Synthesis Pathway 1-4) is also exemplified as a method of manufacturing a 3-hydroxy-6H-benzo [c] chromene-6-one derivative according to the present invention.

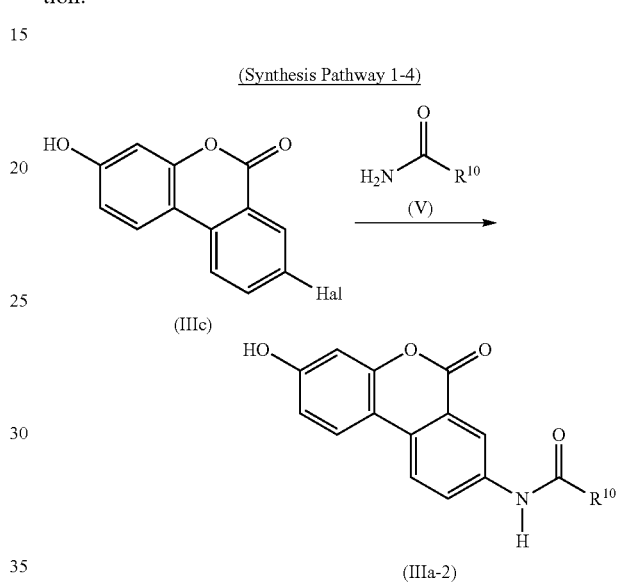

Namely, by subjecting a compound expressed with a formula (IIIc) (a compound in formula (III) above, in which $R^1$, $R^2$, $R^3$, $R^4$, and $R^5$ are each H and $R^6$ is Hal (which means a halogen atom)) and an amide derivative expressed with a formula (V), such as acetamide, to amide coupling reaction in the presence of copper iodide, glycine, and tripotassium phosphate, a compound expressed with a formula (IIIa-2) (a compound in formula (IIIa-1) above, in which $R^9$ is H) can be obtained. It is noted that $R^{10}$ in Synthesis Pathway 1-4 above is the same in definition as in formula (IIa) described above.

At least any of water and an organic solvent is exemplified as a reaction solvent employed in Synthesis Pathway 1-4. As an organic solvent, an alcohol-based solvent such as methanol, ethanol, and tertiary butanol, an ether-based solvent such as tetrahydrofuran, 1,4-dioxane, diethyl ether, diisopropyl ether, and 1,2-dimethoxyethane, an amide-based solvent such as N,N-dimethylacetamide, N,N-dimethylformamide, and N-methyl-2-pyrrolidone, an aromatic hydrocarbon-based solvent such as benzene, toluene, and xylene, dimethylsulfoxide, or the like is exemplified. In addition, these can also be employed as a mixed solvent. An ether-based solvent such as tetrahydrofuran, 1,4-dioxane, diethyl ether, diisopropyl ether, and 1,2-dimethoxyethane or an amide-based solvent such as N,N-dimethylacetamide, N,N-dimethylformamide, and N-methyl-2-pyrrolidone is exemplified as a particularly preferred reaction solvent.

It is noted that the compound expressed with formula (IIIa-2) above can also be synthesized in accordance with the method disclosed in Tetrahedron Letters, 45, 2004, 2311-2315.

A manufacturing example according to the present invention will be shown below. It is noted that these exemplifications are for better understanding of the present invention and do not limit the scope of the present invention.

[Manufacturing Example]

<Reference Example 1: 5-Amino-2-Bromobenzoic Acid (Reference Compound 1)>

In an N,N-dimethylformamide (18.0 mL) solution of 3-aminobenzoic acid (3.00 g, 21.9 mmol), a solution mixture of N,N-dimethylformamide (9.00 mL) and N-bromosuccinimide (4.09 g, 23.0 mmol) was dropped at 5° C. or lower. After stirring for 1 hour at 5° C. or lower, water (60.0 mL) was added, followed by stirring for 12 hours at 5° C. or lower and filtration. A filter residue was further washed with water (5.00 mL) and thereafter dried, to thereby obtain aforementioned Reference Compound 1 (3.68 g, yield 78%) as shown in Table 1 below.

TABLE 1

| 5-amino-2-bromobenzoic acid (Reference Compound 1) 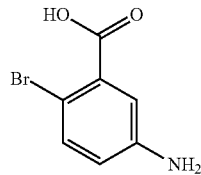 | $^1$H-NMR (400 MHz, DMSO-D$_6$) δ: 5.49 (s, 2H), 6.59 (dd, J = 8.5, 2.9 Hz, 1H), 6.93 (d, J = 2.9 Hz, 1H), 7.25 (d, J = 8.5 Hz, 1H), 13.04 (s, 1H). Yield 78% |
|---|---|

<Reference Example 2-1: 5-(tert-Butoxycarbonylamino)-2-Bromobenzoic Acid (Reference Compound 2-1)>

To a mixture of 5-amino-2-bromobenzoic acid (Reference Compound 1, 25.8 g, 0.119 mol) and water (78.0 mL), 4 M of a sodium hydroxide aqueous solution (30.0 mL, 0.120 mol) and di-tert-butyl-dicarbonate (36.0 mL, 0.157 mol) were added, followed by stirring at room temperature for 40 hours. A reaction solution was ice cooled, neutralized by addition of 1 M of hydrochloric acid (0.120 L, 0.120 mol), and extracted by addition of ethyl acetate (0.400 L) and water (0.250 L). An organic layer was washed with a saturated sodium chloride aqueous solution (0.200 L) and thereafter concentrated, and the obtained solid was washed with a mixed solvent of ethyl acetate and hexane (ethyl acetate:hexane=100:1, 0.200 L) and thereafter dried, to thereby obtain aforementioned Reference Compound 2-1 (34.5 g, yield 92%) as shown in Table 2 below.

TABLE 2

| 5-(tert-butoxycarbonylamino)-2-bromobenzoic acid (Reference Compound 2-1) 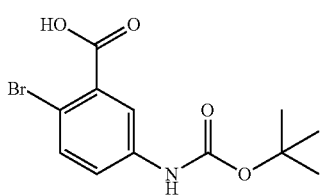 | $^1$H-NMR (400 MHz, DMSO-D$_6$) δ: 1.47 (s, 9H), 7.46 (dd, J = 8.8, 2.6 Hz, 1H), 7.56 (d, J = 8.8 Hz, 1H), 7.92 (d, J = 2.6 Hz, 1H), 9.66 (s, 1H), 13.36 (s, 1H). MS m/z (API-ES) 314 ([M − H]$^-$), 316 ([M + 2 − H]$^-$) Yield 92% |
|---|---|

<Reference Example 2-2: 5-Benzyloxycarbonylamino-2-Bromobenzoic Acid (Reference Compound 2-2)>

To a mixture of 5-amino-2-bromobenzoic acid (Reference Compound 1, 3.00 g, 13.9 mmol) and water (35.0 mL), 4 M of a sodium hydroxide aqueous solution (3.65 mL, 14.6 mmol) and benzyl chloroformate (3.95 mL, 27.8 mmol) were added, followed by stirring at room temperature for 18 hours. A reaction solution was ice cooled, neutralized by addition of 6 M of hydrochloric acid (2.50 mL, 15.0 mmol), and filtered. A filter residue was washed with water (10.0 mL) and toluene (5.00 mL) and thereafter dried, to thereby obtain aforementioned Reference Compound 2-2 (4.29 g, yield 88%) as shown in Table 3 below.

TABLE 3

| 5-benzyloxycarbonylamino-2-bromobenzoic acid (Reference Compound 2-2) | $^1$H-NMR (400 MHz, DMSO-D$_6$) δ: 5.16 (s, 2H), 7.33-7.45 (m, 5H), 7.51 (dd, J = 8.8, 2.6 Hz, 1H), 7.61 (d, J = 8.8 Hz, 1H), 7.91 (d, J = 2.6 Hz, 1H), 10.08 (s, 1H), 13.37 (s, 1H). MS m/z (API-ES) 348 ([M − H]$^-$), 350 ([M + 2 − H]$^-$) Yield 88% |
|---|---|

<Reference Example 2-3: 5-Benzoylamino-2-Bromobenzoic Acid (Reference Compound 2-3)>

To a mixture of 5-amino-2-bromobenzoic acid (3.00 g, 13.9 mmol) and water (35.0 mL), 4 M of a sodium hydroxide aqueous solution (3.65 mL, 14.6 mmol) and benzoic anhydride (4.73 g, 20.9 mmol) were added, followed by stirring at room temperature for 18 hours. A reaction solution was ice cooled, neutralized by addition of 6 M of hydrochloric acid (2.50 mL, 15.0 mmol), and filtered. A filter residue was washed with water (10.0 mL) and toluene (5.00 mL) and thereafter dried, to thereby obtain aforementioned Reference Compound 2-3 (3.80 g, yield 85%) as shown in Table 4 below.

TABLE 4

| 5-benzoylamino-2-bromobenzoic acid (Reference Compound 2-3) | $^1$H-NMR (400 MHz, DMSO-D$_6$) δ: 7.55 (t, J = 7.4 Hz, 2H), 7.62 (tt, J = 7.4, 1.8 Hz, 1H), 7.70 (d, J = 8.8 Hz, 1H), 7.89 (dd, J = 8.8, 2.9 Hz, 1H), 7.96-7.99 (m, 2H), 8.26 (d, J = 2.9 Hz, 1H), 10.50 (s, 1H), 13.41 (s, 1H). MS m/z (API-ES) 320 ([M + H]$^+$), 322 ([M + 2 + H]$^+$) Yield 85% |
|---|---|

<Reference Example 2-4: 5-Acetamide-2-Bromobenzoic Acid. Monohydrate (Reference Compound 2-4)>

To a mixture of 5-amino-2-bromobenzoic acid (Reference Compound 1, 30.5 g, 0.141 mol) and water (0.360 L), 4 M of a sodium hydroxide aqueous solution (37.1 mL, 0.148 mol) and acetic anhydride (20.5 mL, 0.217 mol) were added under ice cooling, followed by stirring at room temperature for 4 hours. A reaction solution was again ice cooled, neutralized by addition of 6 M of hydrochloric acid (26.0 mL, 0.156 mol), and filtered. A filter residue was further washed with water (20 mL) and thereafter dried, to thereby obtain aforementioned Reference Compound 2-4 (38.1 g, yield 98%) as shown in Table 5 below.

TABLE 5

| 5-acetamide-2-bromobenzoic acid • monohydrate (Reference Compound 2-4) 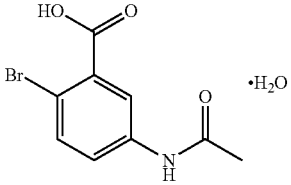 | $^1$H-NMR (400 MHz, DMSO-D$_6$) δ: 2.05 (s, 3H), 7.61-7.64 (m, 2H), 8.02 (d, J = 1.8 Hz, 1H), 10.19 (s, 1H), 13.39 (s, 1H). Yield 98% |
|---|---|

<Reference Example 3: 5-Acetamide-2-(2,4-Dihydroxyphenyl)-Sodium Benzoate (Reference Compound 3)>

To 8-acetamide-3-hydroxy-6H-benzo [c] chromene-6-one (Compound 1-1, 0.128 g, 0.475 mmol), water (5.00 mL) and 4 M of a sodium hydroxide aqueous solution (0.119 mL, 0.476 mmol) were added. After heating and stirring at 60° C. for 3 hours, a reaction solution was filtered and a filtrate was dried, to thereby obtain aforementioned Reference Compound 3 (0.081 g, yield 55%) as shown in Table 6 below.

TABLE 6

| 5-acetamide-2-(2,4-dihydroxyphenyl)-sodium benzoate (Reference Compound 3) 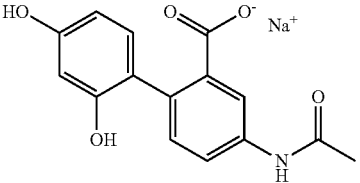 | $^1$H-NMR (500 MHz, D$_2$O) δ: 2.19 (s, 3H), 6.16-6.18 (m, 2H), 6.91 (d, J = 8.9 Hz, 1H), 7.34 (d, J = 8.2 Hz, 1H), 7.40 (d, J = 2.1 Hz, 1H), 7.44 (dd, J = 8.2, 2.1 Hz, 1H). Yield 55% |
|---|---|

<Example 1: 8-Acetamide-3-Hydroxy-6H-Benzo [c] Chromene-6-One (Compound 1-1)>

To a mixture of 5-acetamide-2-bromobenzoic acid.monohydrate (Reference Compound 2-4, 30.0 g, 0.109 mol), resorcinol (38.4 g, 0.349 mol), and sodium carbonate (40.7 g, 0.384 mol), water (300 mL) was added, followed by heating to 50° C. and stirring. Copper iodide (6.64 g, 0.035 mol) was added at 50° C., followed by heating and stirring for 5 hours. A reaction solution was left stand for cooling and filtered, and a filter residue was further washed with water (300 mL) and thereafter dried, to thereby obtain aforementioned Compound 1-1 (23.5 g, yield 80%) as shown in Table 7 below.

TABLE 7

| 8-acetamide-3-hydroxy-6H-benzo [c] chromene-6-one (Compound 1-1) 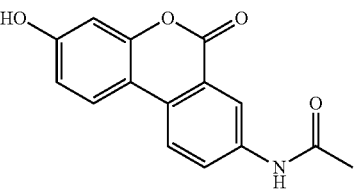 | $^1$H-NMR (400 MHz, DMSO-D$_6$) δ: 2.10 (s, 3H), 6.74 (d, J = 2.4 Hz, 1H), 6.83 (dd, J = 8.8, 2.4 Hz, 1H), 8.00 (dd, J = 8.8, 2.4 Hz, 1H), 8.08 (d, J = 8.8 Hz, 1H), 8.21 (d, J = 8.8 Hz, 1H), 8.50 (d, J = 2.4 Hz, 1H), 10.25 (s, 1H), 10.32 (s, 1H). MS m/z (API-ES) 270 ([M + H]$^+$) Yield 80% |
|---|---|

<Example 2: 8-Acetamide-3-Hydroxy-6H-Benzo [c] Chromene-6-One (Compound 1-1)>

To a mixture of 5-acetamide-2-bromobenzoic acid (Reference Compound 2-4, 1.00 g, 3.88 mmol), resorcinol (1.28 g, 11.6 mmol), and water (10.0 mL), 4 M of a sodium hydroxide aqueous solution (0.969 mL, 3.88 mmol) was added, and after dissolution was confirmed, sodium carbonate (0.945 g, 8.92 mmol) was added, followed by heating to 50° C. and stirring. In succession, copper iodide (0.221 g, 1.16 mmol) was added at 50° C., followed by heating and stirring for 8 hours. Thereafter, a reaction solution was filtered, and a filter residue was further washed with water (10.0 mL) and thereafter dried, to thereby obtain aforementioned Compound 1-1 (0.856 g, yield 82%) as shown in Table 7 above.

<Example 3: 8-Acetamide-3-Hydroxy-6H-Benzo [c] Chromene-6-One (Compound 1-1)>

To a mixture of water (1.50 L), resorcinol (192 g, 1.74 mol), and 5-acetamide-2-bromobenzoic acid (Reference Compound 2-4, 150 g, 0.581 mol), 4 M of a sodium hydroxide aqueous solution (145 mL, 0.580 mol) was added, and after dissolution was confirmed, sodium carbonate (142 g, 1.34 mol) was added, followed by heating to 50° C. and stirring. In succession, copper iodide (33.2 g, 0.174 mol) was added at 50° C., followed by heating and stirring for 15 hours. To a reaction solution, 4 M of a sodium hydroxide aqueous solution (750 mL) and water (3.00 L) were added, and after heating and stirring at 50° C. for 3 hours, filtering was carried out to remove an insoluble. Under ice-cooling, acetonitrile (450 mL) and 12 M of hydrochloric acid (519 mL) were added to a filtrate, followed by stirring for 1 hour. Thereafter, a precipitated solid was filtered and a filter residue was further washed with water (750 mL) and thereafter dried, to thereby obtain aforementioned Compound 1-1 (117 g, yield 75%) as shown in Table 7 above.

<Example 4: 8-Acetamide-3-Hydroxy-6H-Benzo [c] Chromene-6-One (Compound 1-1)>

To 5-acetamide-2-(2,4-dihydroxyphenyl)-sodium benzoate (Reference Compound 3, 0.435 g, 1.41 mmol), water (15 mL) and 6 M of hydrochloric acid (0.704 mL, 4.22 mmol) were added. After stirring at room temperature for 1 hour and 30 minutes, a reaction solution was filtered, and a filter residue was further washed with water (7.50 mL) and thereafter dried, to thereby obtain aforementioned Compound 1-1 (0.319 g, yield 84%) as shown in Table 7 above.

In the following, Reference Compound 2-2, 2-3, 2-bromo-5-fluorobenzoic acid (a commercially available compound), 2-1, 2-bromo-3-nitrobenzoic acid (a commercially available compound), 2-bromo-4-methylbenzoic acid (a commercially available compound), 2-bromobenzoic acid (a commercially available compound), 4-bromoisophthalic acid (a commercially available compound), 2-bromo-5-iodobenzoic acid (a commercially available compound), 2,5-dibromobenzoic acid (a commercially available compound), or 2-bromo-5-nitrobenzoic acid (a commercially available compound) was employed to obtain Compounds 1-2, 1-3, 1-4, 1-5, 1-6, 1-7, 1-8, 1-9, 1-10, 1-11, and 1-12, in conformity with the method of manufacturing Compound 1-1 (the method described in Example 1).

TABLE 8

| | |
|---|---|
| 8-benzyloxycarbonylamino-3-hydroxy-6H-benzo [c] chromene-6-one (Compound 1-2) 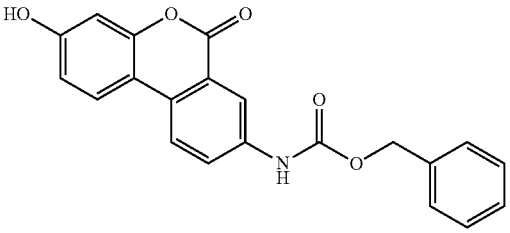 | ¹H-NMR (400 MHz, DMSO-D₆) δ: 5.20 (s, 2H), 6.74 (d, J = 2.2 Hz, 1H), 6.83 (dd, J = 8.8, 2.2 Hz, 1H), 7.34-7.47 (m, 5H), 7.91 (dd, J = 8.8, 2.2 Hz, 1H), 8.07 (d, J = 8.8 Hz, 1H), 8.21 (d, J = 8.8 Hz, 1H), 8.38 (d, J = 2.2 Hz, 1H), 10.20 (s, 1H), 10.24 (s, 1H). MS m/z (API-ES) 360 ([M − H]⁻) Yield 75% |
| 8-benzoylamino-3-hydroxy-6H-benzo [c] chromene-6-one (Compound 1-3) 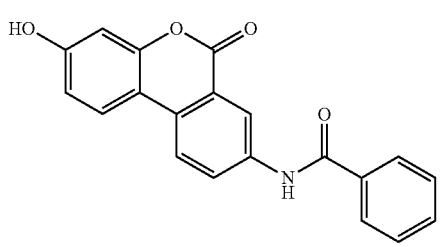 | ¹H-NMR (400 MHz, DMSO-D₆) δ: 6.77 (s, 1H), 6.85 (d, J = 8.0 Hz, 1H), 7.57 (t, J = 7.3 Hz, 2H), 7.63 (t, J = 7.3 Hz, 1H), 8.01 (d, J = 7.1 Hz, 2H), 8.13 (d, J = 8.0 Hz, 1H), 8.28 (s, 2H), 8.73 (s, 1H), 10.29 (s, 1H), 10.62 (s, 1H). MS m/z (API-ES) 332 ([M + H]⁺) Yield 59% |

TABLE 9

| | |
|---|---|
| 8-fluoro-3-hydroxy-6H-benzo [c] chromene-6-one (Compound 1-4) 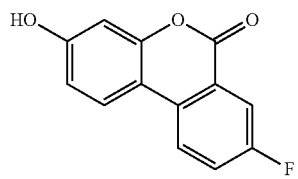 | ¹H-NMR (500 MHz, DMSO-D₆) δ: 6.77 (s, 1H), 6.85 (d, J = 8.2 Hz, 1H), 7.80 (td, J = 8.7, 3.2 Hz, 1H), 7.89 (dd, J = 8.7, 3.2 Hz, 1H), 8.16 (d, J = 8.2 Hz, 1H), 8.36 (dd, J = 8.7, 3.2 Hz, 1H), 10.36 (s, 1H). MS m/z (API-ES) 229 ([M − H]⁻) Yield 91% |
| 8-(tert-butoxycarbonylamino)-3-hydroxy-6H-benzo [c] chromene-6-one (Compound 1-5) 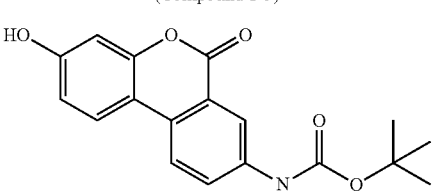 | ¹H-NMR (400 MHz, DMSO-D₆) δ: 1.51 (s, 9H), 6.74 (d, J = 2.2 Hz, 1H), 6.82 (dd, J = 8.8, 2.2 Hz, 1H), 7.86 (dd, J = 8.8, 2.2 Hz, 1H), 8.06 (d, J = 8.8 Hz, 1H), 8.17 (d, J = 8.8 Hz, 1H), 8.41 (d, J = 2.2 Hz, 1H), 9.79 (s, 1H), 10.22 (s, 1H). MS m/z (API-ES) 328 ([M + H]⁺) Yield 73% |

TABLE 10

| Compound | ¹H-NMR |
|---|---|
| 3-hydroxy-10-nitro-6H-benzo [c] chromene-6-one (Compound 1-6) | ¹H-NMR (400 MHz, DMSO-D₆) δ: 6.81 (d, J = 2.7 Hz, 1H), 6.84 (dd, J = 9.0, 2.7 Hz, 1H), 7.34 (d, J = 9.0 Hz, 1H), 7.73 (t, J = 7.9 Hz, 1H), 8.27 (dd, J = 7.9, 1.3 Hz, 1H), 8.45 (dd, J = 7.9, 1.3 Hz, 1H), 10.74 (s, 1H). MS m/z (API-ES) 256 ([M − H]⁻) Yield 63% |
| 3-hydroxy-9-methyl-6H-benzo [c] chromene-6-one (Compound 1-7) | ¹H-NMR (400 MHz, DMSO-D₆) δ: 3.33 (s, 3H), 6.74 (d, J = 2.4 Hz, 1H), 6.84 (dd, J = 8.8, 2.4 Hz, 1H), 7.39 (d, J = 8.1 Hz, 1H), 8.08 (d, J = 8.1 Hz, 1H), 8.10 (s, 1H), 8.15 (d, J = 8.8 Hz, 1H), 10.32 (s, 1H). MS m/z (API-ES) 227 ([M + H]⁺) Yield 100% |

TABLE 11

| Compound | ¹H-NMR |
|---|---|
| 3-hydroxy-6H-benzo [c] chromene-6-one (Compound 1-8) | ¹H-NMR (400 MHz, DMSO-D₆) δ: 6.76 (s, 1H), 6.85 (d, J = 8.0 Hz, 1H), 7.57 (t, J = 7.3 Hz, 1H), 7.89 (t, J = 7.3 Hz, 1H), 8.18 (t, J = 7.3 Hz, 2H), 8.27 (d, J = 8.0 Hz, 1H), 10.35 (s, 1H). MS m/z (API-ES) 213 ([M + H]⁺) Yield 100% |
| 8-carboxyl-3-hydroxy-6H-benzo [c] chromene-6-one (Compound 1-9) | ¹H-NMR (400 MHz, DMSO-D₆) δ: 6.78 (d, J = 2.2 Hz, 1H), 6.88 (dd, J = 8.8, 2.2 Hz, 1H), 8.22 (d, J = 8.8 Hz, 1H), 8.32 (dd, J = 8.4, 1.8 Hz, 1H), 8.37 (d, J = 8.4 Hz, 1H), 8.68 (d, J = 1.8 Hz, 1H), 10.56 (s, 1H), 13.25 (s, 1H). MS m/z (API-ES) 255 ([M − H]⁻) Yield 39% |

TABLE 12

| Compound | ¹H-NMR |
|---|---|
| 8-iodo-3-hydroxy-6H-benzo [c] chromene-6-one (Compound 1-10) | ¹H-NMR (400 MHz, DMSO-D₆) δ: 6.75 (d, J = 2.4 Hz, 1H), 6.85 (dd, J = 8.8, 2.4 Hz, 1H), 8.06 (d, J = 8.5 Hz, 1H), 8.16 (d, J = 8.8 Hz, 1H), 8.18 (dd, J = 8.5, 1.7 Hz, 1H), 8.43 (d, J = 1.7 Hz, 1H), 10.43 (s, 1H). MS m/z (API-ES) 339 ([M + H]⁺) Yield 74% |
| 8-bromo-3-hydroxy-6H-benzo [c] chromene-6-one (Compound 1-11) | ¹H-NMR (500 MHz, DMSO-D₆) δ: 6.76 (d, J = 2.4 Hz, 1H), 6.85 (dd, J = 8.9, 2.4 Hz, 1H), 8.05 (dd, J = 8.9, 2.4 Hz, 1H), 8.18 (d, J = 8.9 Hz, 1H), 8.24 (d, J = 8.9 Hz, 1H), 8.25 (d, J = 2.4 Hz, 1H), 10.45 (s, 1H). MS m/z (API-ES) 291 ([M + H]⁺), 293 ([M + 2 + H]⁺) Yield 87% |

TABLE 13

| Compound | ¹H-NMR |
|---|---|
| 8-nitro-3-hydroxy-6H-benzo [c] chromene-6-one (Compound 1-12) | ¹H-NMR (400 MHz, DMSO-D₆) δ: 6.81 (d, J = 2.3 Hz, 1H), 6.91 (dd, J = 8.8, 2.3 Hz, 1H), 8.29 (d, J = 8.8 Hz, 1H), 8.50 (d, J = 9.0 Hz, 1H), 8.61 (dd, J = 9.0, 2.5 Hz, 1H), 8.82 (d, J = 2.5 Hz, 1H), 10.76 (s, 1H). MS m/z (API-ES) 256 ([M − H]⁻) Yield 65% |

<Comparative Example 1: 8-Acetamide-3-Hydroxy-6H-Benzo [c] Chromene-6-One (Compound 1-1)>

With the method described in NPD 1, Compound 1-1 shown in Table 7 above was manufactured (Comparative Example 1). To 5-acetamide-2-bromobenzoic acid.monohydrate (Reference Compound 2-4, 0.221 g, 0.801 mmol), resorcinol (0.179 g, 1.63 mmol), and sodium hydroxide (0.075 g, 1.88 mmol), water (1.00 mL) was added, followed by heating to 100° C. and stirring. Furthermore, a 5% copper sulfate aqueous solution (0.337 mL, 0.106 mmol) was added, followed by heating and stirring for 1 hour. A reaction solution was left stand for cooling, thereafter cooled, neutralized with acetic acid (0.112 mL, 1.96 mmol), and filtered. A filter residue was further washed with water (3.00 mL) and thereafter dried, to thereby obtain aforementioned Compound 1-1 (0.084 g, yield 39%).

<Comparative Example 2: 8-Acetamide-3-Hydroxy-6H-Benzo [c] Chromene-6-One (Compound 1-1)>

With the method described in NPD 1, under a condition of a reaction temperature of 50° C., Compound 1-1 shown in Table 7 above was manufactured (Comparative Example 2). To 5-acetamide-2-bromobenzoic acid.monohydrate (Reference Compound 2-4, 0.200 g, 0.724 mmol) and resorcinol (0.160 g, 1.45 mmol), 4 M of a sodium hydroxide aqueous solution (0.398 mL, 1.59 mmol) and water (0.600 mL) were added, followed by heating and stirring at 50° C. Furthermore, a 10% copper sulfate aqueous solution (0.116 mL, 0.073 mmol) was added, followed by heating and stirring for 5 hours. A reaction solution was left stand for cooling, thereafter cooled, neutralized with 6 M of hydrochloric acid (0.267 mL, 1.60 mmol), and filtered. A filter residue was further washed with water (5.00 mL) and ethanol (5.00 mL) and thereafter dried, to thereby obtain aforementioned Compound 1-1 (0.067 g, yield 34%).

Reference Compounds 2-4, 2-2, 2-3, 2-1 and 2-bromo-3-nitrobenzoic acid (a commercially available compound) or 2-bromo-5-nitrobenzoic acid (a commercially available compound) were employed to obtain Compounds 1-2, 1-3, 1-5, 1-6, and 1-12 in conformity with the manufacturing method in Comparative Example 1.

Table 14 shows yield (%) in a case of using the method of manufacturing Compounds 1-1, 1-2, 1-3, 1-5, 1-6, and 1-12 according to the present invention (the method described in Example 1) and yield (%) in a case of using the manufacturing method described in NPD 1 (the method described in Comparative Example 1).

TABLE 14

| Compound | Yield (%) of Each Compound in Using Manufacturing Method According to the Present Invention | Yield (%) of Each Compound in Using Manufacturing Method Described in NPD 1 |
|---|---|---|
| 1-1 | 80 | 39 |
| 1-2 | 75 | 36 |
| 1-3 | 59 | 24 |
| 1-5 | 73 | 33 |
| 1-6 | 63 | 9 |
| 1-12 | 65 | Trace Amount |

INDUSTRIAL APPLICABILITY

According to the present invention, a 3-hydroxy-6H-benzo[c]chromene-6-one derivative useful as an intermediate product of a 1,2-dihydroquinoline derivative having glucocorticoid receptor binding activities or as a selective estrogen β receptor agonist can be manufactured under a milder condition at more satisfactory yield than with a conventionally known manufacturing method, and it is industrially useful. In addition, an inexpensive reagent such as sodium carbonate or copper iodide can be applied to the present inventive method and therefore the present inventive method is cost-effective in implementing industrial manufacturing.

The invention claimed is:

1. A method of manufacturing comprising reacting a compound or a salt thereof expressed by formula (I) below

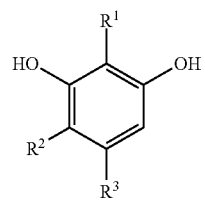

(I)

wherein $R^1$, $R^2$, or $R^3$ represents a hydrogen atom, a lower alkyl group, a hydroxy group, or a lower alkoxy group, and a compound or a salt thereof expressed by formula (II) below

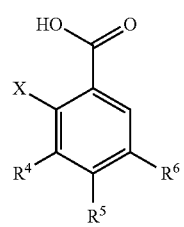

(II)

wherein $R^4$ represents a hydrogen atom, a lower alkyl group, a nitro group, an amino group, or a lower alkylamino group, $R^5$ represents a hydrogen atom or a lower alkyl group, $R^6$ represents a hydrogen atom, a halogen atom, a lower alkyl group, a carboxyl group, a nitro group, or —$NR^aR^b$, wherein $R^a$ and $R^b$ are the same or different and each represents a hydrogen atom, a formyl group, a lower alkyl carbonyl group, a lower alkenyl carbonyl group, a lower cycloalkyl carbonyl group, an aryl carbonyl group, a carboxyl group, a lower alkoxy carbonyl group, a lower alkenyloxycarbonyl group, a lower cycloalkyloxycarbonyl group, an aryloxy carbonyl group, or an arylalkyloxycarbonyl group, and X represents a halogen atom, a lower alkylsulfonyloxy group, or an aryl sulfonyloxy group, to produce, a compound or a salt thereof expressed by formula (III) below

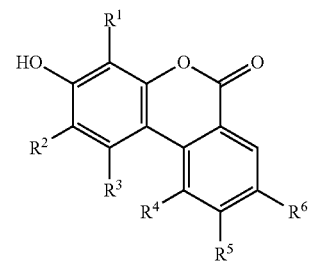

(III)

wherein $R^1$, $R^2$, $R^3$, $R^4$, $R^5$, or $R^6$ have the same definitions as in formula (I) and formula (II) above, wherein the compound or the salt thereof expressed by formula (I) above and the compound or the salt thereof expressed by formula (II) above are reacted in the presence of carbonate and copper salt or in presence of hydroxide salt, carbonate, and copper salt.

2. A method of manufacturing comprising reacting a compound or a salt thereof expressed with a formula (Ia) below

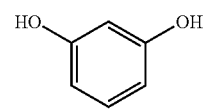

(Ia)

and a compound or a salt thereof expressed by formula (II a) below

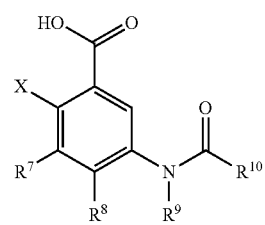

(IIa)

wherein $R^7$ represents a hydrogen atom, a lower alkyl group, a nitro group, an amino group, or a lower alkylamino group, $R^8$ represents a hydrogen atom or a lower alkyl group, $R^9$ represents a hydrogen atom or a lower alkyl group, $R^{10}$ represents a hydrogen atom, a lower alkyl group, a lower alkenyl group, a lower cycloalkyl group, an aryl group, a hydroxy group, a lower alkoxy group, a lower alkenyloxy group, a lower cycloalkyloxy group, an aryloxy group, or an arylalkyloxy group, and X representing a halogen atom, a lower alkylsulfonyloxy group, or an aryl sulfonyloxy group, to produce, a compound or a salt thereof expressed by formula (IIIa) below

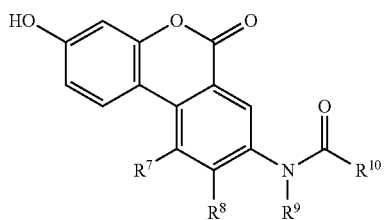

(IIIa)

wherein $R^7$, $R^8$, $R^9$, or $R^{10}$ have the same definitions as in formula (IIa), wherein the reaction is conducted in the presence of carbonate and copper salt or in the presence of hydroxide salt, carbonate, and copper salt.

3. The method according to claim 2, wherein in formula (IIIa), $R^7$, $R^8$, and $R^9$ each represent a hydrogen atom and $R^{10}$ represents a lower alkyl group, an aryl group, a lower alkoxy group, or an arylalkyloxy group.

4. The method according to claim 2, wherein in formula (IIIa), $R^7$, $R^8$, and $R^9$ each represent a hydrogen atom and $R^{10}$ represents a methyl group, a phenyl group, a tert-butoxy group, or a benzyloxy group.

5. The method according to claim 2, wherein the compound or the salt thereof expressed by formula (IIIa) is a compound or a salt thereof selected from the group consisting of 8-acetamide-3-hydroxy-6H-benzo [c] chromene-6-one, 8-benzyloxycarbonylamino-3-hydroxy-6H-benzo [c] chromene-6-one, 8-benzoylamino-3-hydroxy-6H-benzo [c] chromene-6-one, and 8-(tert-butoxycarbonylamino)-3-hydroxy-6H-benzo [c] chromene-6-one.

6. A method of manufacturing comprising reacting a compound or a salt thereof expressed by formula (I) below

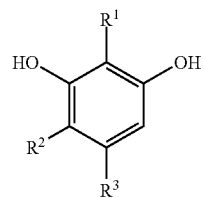

(I)

wherein $R^1$, $R^2$, or $R^3$ represents a hydrogen atom, a lower alkyl group, a hydroxy group, or a lower alkoxy group, and a compound or a salt thereof expressed by formula (II) below

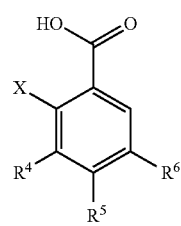

(II)

wherein $R^4$ represents a hydrogen atom, a lower alkyl group, a nitro group, an amino group, or a lower alkylamino group, $R^5$ represents a hydrogen atom or a lower alkyl group, $R^6$ represents a hydrogen atom, a halogen atom, a lower alkyl group, a carboxyl group, a nitro group, or —$NR^aR^b$, wherein $R^a$ and $R^b$ are the same or different and each represents a hydrogen atom, a formyl group, a lower alkyl carbonyl group, a lower alkenyl carbonyl group, a lower cycloalkyl carbonyl group, an aryl carbonyl group, a carboxyl group, a lower alkoxy carbonyl group, a lower alkenyloxycarbonyl group, a lower cycloalkyloxycarbonyl group, an aryloxy carbonyl group, or an arylalkyloxycarbonyl group, and X represents a halogen atom, a lower alkylsulfonyloxy group, or an aryl sulfonyloxy group, in presence of carbonate and copper salt or in presence of hydroxide salt, carbonate, and copper salt to produce, a compound or a salt thereof expressed by formula (III) below

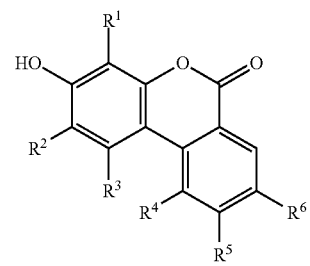

(III)

wherein $R^1$, $R^2$, $R^3$, $R^4$, $R^5$, or $R^6$ have the same definitions as in formula (I) and formula (II), and reacting the compound or the salt thereof expressed by formula (III) above to react with hydroxide salt for conversion to a compound or a salt thereof expressed by formula (IV) below

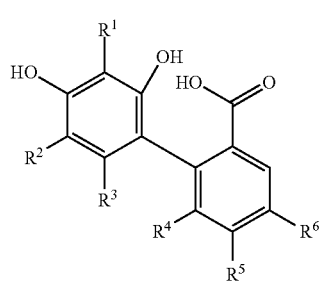

(IV)

wherein $R^1$, $R^2$, $R^3$, $R^4$, $R^5$, or $R^6$ have the same definitions as in formula (I) and formula (II), and then reacting the compound or the salt thereof expressed by formula (IV) above with an acid.

7. A method of manufacturing comprising reacting, a compound or a salt thereof expressed by formula (Ia) below

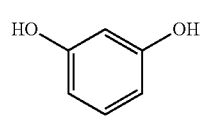
(Ia)

and a compound or a salt thereof expressed by formula (IIa) below

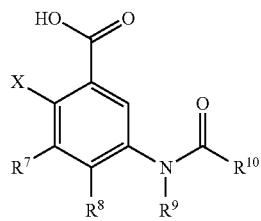
(IIa)

wherein $R^7$ represents a hydrogen atom, a lower alkyl group, a nitro group, an amino group, or a lower alkylamino group, $R^8$ represents a hydrogen atom or a lower alkyl group, $R^9$ represents a hydrogen atom or a lower alkyl group, $R^{10}$ represents a hydrogen atom, a lower alkyl group, a lower alkenyl group, a lower cycloalkyl group, an aryl group, a hydroxy group, a lower alkoxy group, a lower alkenyloxy group, a lower cycloalkyloxy group, an aryloxy group, or an arylalkyloxy group, and X representing a halogen atom, a lower alkylsulfonyloxy group, or an aryl sulfonyloxy group, in presence of carbonate and copper salt or in presence of hydroxide salt, carbonate, and copper salt to produce, a compound or a salt thereof expressed by formula (IIIa) below

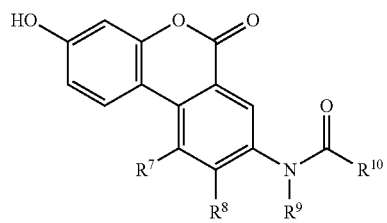
(IIIa)

wherein $R^7$, $R^8$, $R^9$, or $R^{10}$ have the same definitions as in formula (IIa), and reacting the compound or the salt thereof expressed by formula (IIIa) above to react with hydroxide salt for conversion to a compound or a salt thereof expressed by formula (IVa) below

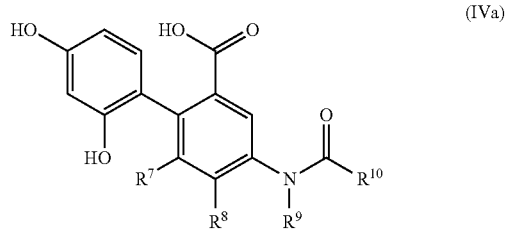
(IVa)

wherein $R^7$, $R^8$, $R^9$, or $R^{10}$ have the same definitions as in formula (IIa), and then reacting the compound or the salt thereof expressed with formula (IVa) above with an acid.

8. The method according to claim 7, wherein
in formula (IIIa), $R^7$, $R^8$, and $R^9$ each represent a hydrogen atom and $R^{10}$ represents a lower alkyl group, an aryl group, a lower alkoxy group, or an arylalkyloxy group.

9. The method according to claim 7, wherein
in formula (IIIa), $R^7$, $R^8$, and $R^9$ each represent a hydrogen atom and $R^{10}$ represents a methyl group, a phenyl group, a tert-butoxy group, or a benzyloxy group.

10. The method according to claim 7, wherein
the compound or the salt thereof expressed with formula IIIa) is a compound or a salt thereof selected from the group consisting of 8-acetamide-3-hydroxy-6H-benzo [c] chromene-6-one, 8-benzyloxycarbonylamino-3-hydroxy-6H-benzo [c] chromene-6-one, 8-benzoylamino-3-hydroxy-6H-benzo [c] chromene-6-one, and 8-(tert-butoxycarbonylamino)-3-hydroxy-6H-benzo [c] chromene-6-one.

\* \* \* \* \*